(12) United States Patent
Mazar et al.

(10) Patent No.: US 9,451,897 B2
(45) Date of Patent: Sep. 27, 2016

(54) BODY ADHERENT PATCH WITH ELECTRONICS FOR PHYSIOLOGIC MONITORING

(75) Inventors: Scott T. Mazar, Woodbury, MN (US); Senthil Swaminathan, Saint Paul, MN (US); Jonathan Engel, Minneapolis, MN (US); Arthur Lai, Minnetonka, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 604 days.

(21) Appl. No.: 12/958,910

(22) Filed: Dec. 2, 2010

(65) Prior Publication Data

US 2011/0144470 A1 Jun. 16, 2011

Related U.S. Application Data

(60) Provisional application No. 61/286,075, filed on Dec. 14, 2009.

(51) Int. Cl.
*A61B 5/04* (2006.01)
*A61B 5/0408* (2006.01)
(Continued)

(52) U.S. Cl.
CPC ....... *A61B 5/04087* (2013.01); *A61B 5/04085* (2013.01); *A61B 5/04325* (2013.01); *A61B 5/6833* (2013.01); *A61B 5/0006* (2013.01); *A61B 2560/0412* (2013.01); *Y10T 29/49117* (2015.01)

(58) Field of Classification Search
CPC .................. A61B 5/04; A61B 5/6833; A61B 2560/0412; A61B 5/0006; A61B 5/0205; A61N 1/0492; A61N 1/0476

USPC ............... 600/372, 382, 384, 386, 390–393, 600/508–509
See application file for complete search history.

(56) References Cited

U.S. PATENT DOCUMENTS

| 834,261 A | 10/1906 | Chambers |
| 2,087,124 A | 7/1937 | Smith et al. |

(Continued)

FOREIGN PATENT DOCUMENTS

| WO | WO 00/79255 A1 | 12/2000 |
| WO | WO 02/092101 A1 | 11/2002 |

(Continued)

OTHER PUBLICATIONS

"Acute Decompensated Heart Failure" —Wikipedia Entry, downloaded from: <http://en.wikipedia.org/wiki/Acute_decompensated_heart_failure>, entry page created in 2008, 6 pages total.

(Continued)

*Primary Examiner* — Joseph Stoklosa
*Assistant Examiner* — Brian M Antiskay
(74) *Attorney, Agent, or Firm* — Billion & Armitage; Michael A. Collins

(57) ABSTRACT

In one configuration, an adherent device to adhere to a skin of a subject includes a stretchable base layer having an upper side and a lower side and an adhesive coating on the lower side to adhere the base layer to the skin of the subject. The base layer has at least two openings extending therethrough, each of the at least two openings having a size. The adherent device also includes a stretchable covering layer positioned above and adhered to the base layer with an adhesive to define at least two pockets. The adherent device also includes at least two gels, each gel having a size larger than the size of openings to retain the gel substantially within the pocket, and a circuit carrier supported with the stretchable base layer to measure at least one physiologic signal of the subject. Other configurations and methods are also claimed.

21 Claims, 7 Drawing Sheets

(51) Int. Cl.
*A61B 5/0432* (2006.01)
*A61B 5/00* (2006.01)

(56) References Cited

U.S. PATENT DOCUMENTS

| | | | |
|---|---|---|---|
| 2,184,511 A | 12/1939 | Bagno et al. | |
| 3,170,459 A | 2/1965 | Phipps et al. | |
| 3,232,291 A | 2/1966 | Parker | |
| 3,370,459 A | 2/1968 | Cescati | |
| 3,517,999 A | 6/1970 | Weaver | |
| 3,620,216 A | 11/1971 | Szymanski | |
| 3,677,260 A | 7/1972 | Funfstuck et al. | |
| 3,805,769 A | 4/1974 | Sessions | |
| 3,845,757 A | 11/1974 | Weyer | |
| 3,874,368 A | 4/1975 | Asrican | |
| 3,882,853 A | 5/1975 | Gofman et al. | |
| 3,942,517 A | 3/1976 | Bowles et al. | |
| 3,972,329 A | 8/1976 | Kaufman | |
| 4,008,712 A | 2/1977 | Nyboer | |
| 4,024,312 A | 5/1977 | Korpman | |
| 4,077,406 A | 3/1978 | Sandhage et al. | |
| 4,102,331 A * | 7/1978 | Grayzel et al. | 600/385 |
| 4,121,573 A | 10/1978 | Crovella et al. | |
| 4,141,366 A | 2/1979 | Cross, Jr. et al. | |
| RE30,101 E | 9/1979 | Kubicek et al. | |
| 4,185,621 A | 1/1980 | Morrow | |
| 4,216,462 A | 8/1980 | McGrath et al. | |
| 4,300,575 A | 11/1981 | Wilson | |
| 4,308,872 A | 1/1982 | Watson et al. | |
| 4,358,678 A | 11/1982 | Lawrence | |
| 4,409,983 A | 10/1983 | Albert | |
| 4,450,527 A | 5/1984 | Sramek | |
| 4,451,254 A | 5/1984 | Dinius et al. | |
| 4,478,223 A | 10/1984 | Allor | |
| 4,498,479 A | 2/1985 | Martio et al. | |
| 4,522,211 A | 6/1985 | Bare et al. | |
| 4,661,103 A | 4/1987 | Harman | |
| 4,664,129 A | 5/1987 | Helzel et al. | |
| 4,669,480 A | 6/1987 | Hoffman | |
| 4,673,387 A | 6/1987 | Phillips et al. | |
| 4,674,511 A | 6/1987 | Cartmell | |
| 4,681,118 A | 7/1987 | Asai et al. | |
| 4,692,685 A | 9/1987 | Blaze | |
| 4,699,146 A | 10/1987 | Sieverding | |
| 4,721,110 A | 1/1988 | Lampadius | |
| 4,730,611 A | 3/1988 | Lamb | |
| 4,781,200 A | 11/1988 | Baker | |
| 4,793,362 A | 12/1988 | Tedner | |
| 4,838,273 A | 6/1989 | Cartmell | |
| 4,838,279 A | 6/1989 | Fore | |
| 4,850,370 A | 7/1989 | Dower | |
| 4,880,004 A | 11/1989 | Baker, Jr. et al. | |
| 4,895,163 A | 1/1990 | Libke et al. | |
| 4,911,175 A | 3/1990 | Shizgal | |
| 4,945,916 A | 8/1990 | Kretschmer et al. | |
| 4,955,381 A | 9/1990 | Way et al. | |
| 4,966,158 A | 10/1990 | Honma et al. | |
| 4,981,139 A | 1/1991 | Pfohl | |
| 4,988,335 A | 1/1991 | Prindle et al. | |
| 4,989,612 A | 2/1991 | Fore | |
| 5,001,632 A | 3/1991 | Hall-Tipping | |
| 5,012,810 A | 5/1991 | Strand et al. | |
| 5,025,791 A | 6/1991 | Niwa | |
| 5,027,824 A | 7/1991 | Dougherty et al. | |
| 5,050,612 A | 9/1991 | Matsumura | |
| 5,063,937 A | 11/1991 | Ezenwa et al. | |
| 5,080,099 A | 1/1992 | Way et al. | |
| 5,083,563 A | 1/1992 | Collins | |
| 5,086,781 A | 2/1992 | Bookspan | |
| 5,113,869 A | 5/1992 | Nappholz et al. | |
| 5,125,412 A | 6/1992 | Thornton | |
| 5,133,355 A | 7/1992 | Strand et al. | |
| 5,140,985 A | 8/1992 | Schroeder et al. | |
| 5,150,708 A | 9/1992 | Brooks | |
| 5,168,874 A | 12/1992 | Segalowitz | |
| 5,226,417 A | 7/1993 | Swedlow et al. | |
| 5,241,300 A | 8/1993 | Buschmann | |
| 5,257,627 A | 11/1993 | Rapoport | |
| 5,271,411 A | 12/1993 | Ripley et al. | |
| 5,273,532 A | 12/1993 | Niezink et al. | |
| 5,282,840 A | 2/1994 | Hudrlik | |
| 5,291,013 A | 3/1994 | Nafarrate et al. | |
| 5,297,556 A | 3/1994 | Shankar | |
| 5,301,677 A | 4/1994 | Hsung | |
| 5,319,363 A | 6/1994 | Welch et al. | |
| 5,331,966 A | 7/1994 | Bennett et al. | |
| 5,335,664 A | 8/1994 | Nagashima | |
| 5,343,869 A | 9/1994 | Pross et al. | |
| 5,353,793 A | 10/1994 | Bornn | |
| 5,362,069 A | 11/1994 | Hall-Tipping | |
| 5,375,604 A | 12/1994 | Kelly et al. | |
| 5,406,945 A | 4/1995 | Riazzi et al. | |
| 5,411,530 A | 5/1995 | Akhtar | |
| 5,437,285 A | 8/1995 | Verrier et al. | |
| 5,443,073 A | 8/1995 | Wang et al. | |
| 5,449,000 A | 9/1995 | Libke et al. | |
| 5,450,845 A | 9/1995 | Axelgaard | |
| 5,454,377 A | 10/1995 | Dzwonczyk et al. | |
| 5,464,012 A | 11/1995 | Falcone | |
| 5,469,859 A | 11/1995 | Tsoglin et al. | |
| 5,482,036 A | 1/1996 | Diab et al. | |
| 5,503,157 A | 4/1996 | Sramek | |
| 5,511,548 A | 4/1996 | Riazzi et al. | |
| 5,511,553 A | 4/1996 | Segalowitz | |
| 5,518,001 A | 5/1996 | Snell | |
| 5,523,742 A | 6/1996 | Simkins et al. | |
| 5,529,072 A | 6/1996 | Sramek | |
| 5,544,661 A | 8/1996 | Davis et al. | |
| 5,558,638 A | 9/1996 | Evers et al. | |
| 5,560,368 A | 10/1996 | Berger | |
| 5,564,429 A | 10/1996 | Bornn et al. | |
| 5,564,434 A | 10/1996 | Halperin et al. | |
| 5,566,671 A | 10/1996 | Lyons | |
| 5,575,284 A | 11/1996 | Athan et al. | |
| 5,607,454 A | 3/1997 | Cameron et al. | |
| 5,632,272 A | 5/1997 | Diab et al. | |
| 5,634,468 A | 6/1997 | Platt et al. | |
| 5,642,734 A | 7/1997 | Ruben et al. | |
| 5,673,704 A | 10/1997 | Marchlinski et al. | |
| 5,678,562 A | 10/1997 | Sellers | |
| 5,687,717 A | 11/1997 | Halpern et al. | |
| 5,718,234 A | 2/1998 | Warden et al. | |
| 5,724,025 A | 3/1998 | Tavori | |
| 5,738,107 A | 4/1998 | Martinsen et al. | |
| 5,748,103 A | 5/1998 | Flach et al. | |
| 5,767,791 A | 6/1998 | Stoop et al. | |
| 5,769,793 A | 6/1998 | Pincus et al. | |
| 5,772,508 A | 6/1998 | Sugita et al. | |
| 5,772,586 A | 6/1998 | Heinonen et al. | |
| 5,778,882 A | 7/1998 | Raymond et al. | |
| 5,788,643 A | 8/1998 | Feldman | |
| 5,803,915 A | 9/1998 | Kremenchugsky et al. | |
| 5,807,272 A | 9/1998 | Kun | |
| 5,814,079 A | 9/1998 | Kieval et al. | |
| 5,817,035 A | 10/1998 | Sullivan | |
| 5,833,603 A | 11/1998 | Kovacs et al. | |
| 5,836,990 A | 11/1998 | Li | |
| 5,855,614 A | 1/1999 | Stevens et al. | |
| 5,860,860 A | 1/1999 | Clayman | |
| 5,862,802 A | 1/1999 | Bird | |
| 5,862,803 A | 1/1999 | Besson et al. | |
| 5,865,733 A | 2/1999 | Malinouskas et al. | |
| 5,876,353 A | 3/1999 | Riff | |
| 5,904,708 A | 5/1999 | Goedeke | |
| 5,935,079 A | 8/1999 | Swanson et al. | |
| 5,941,831 A | 8/1999 | Turcott | |
| 5,944,659 A | 8/1999 | Flach et al. | |
| 5,949,636 A | 9/1999 | Johnson et al. | |
| 5,957,854 A | 9/1999 | Besson et al. | |
| 5,957,861 A | 9/1999 | Combs et al. | |
| 5,964,703 A | 10/1999 | Goodman et al. | |
| 5,970,986 A | 10/1999 | Bolz et al. | |
| 5,984,102 A | 11/1999 | Tay | |
| 5,987,352 A | 11/1999 | Klein et al. | |

(56) References Cited

U.S. PATENT DOCUMENTS

| | | | |
|---|---|---|---|
| 6,007,532 A | 12/1999 | Netherly | |
| 6,027,523 A | 2/2000 | Schmieding | |
| 6,045,513 A | 4/2000 | Stone et al. | |
| 6,047,203 A | 4/2000 | Sackner et al. | |
| 6,047,259 A | 4/2000 | Campbell et al. | |
| 6,049,730 A | 4/2000 | Kristbjarnarson | |
| 6,050,267 A | 4/2000 | Nardella et al. | |
| 6,050,951 A | 4/2000 | Friedman et al. | |
| 6,052,615 A | 4/2000 | Feild et al. | |
| 6,080,106 A | 6/2000 | Lloyd et al. | |
| 6,081,735 A | 6/2000 | Diab et al. | |
| 6,095,991 A | 8/2000 | Krausman et al. | |
| 6,102,856 A | 8/2000 | Groff et al. | |
| 6,104,949 A | 8/2000 | Pitts Crick et al. | |
| 6,112,224 A | 8/2000 | Peifer et al. | |
| 6,117,077 A | 9/2000 | Del Mar et al. | |
| 6,125,297 A | 9/2000 | Siconolfi | |
| 6,129,744 A | 10/2000 | Boute | |
| 6,141,575 A | 10/2000 | Price | |
| 6,144,878 A | 11/2000 | Schroeppel et al. | |
| 6,164,284 A | 12/2000 | Schulman et al. | |
| 6,181,963 B1 * | 1/2001 | Chin et al. | 604/20 |
| 6,185,452 B1 | 2/2001 | Schulman et al. | |
| 6,190,313 B1 | 2/2001 | Hinkle | |
| 6,190,324 B1 | 2/2001 | Kieval et al. | |
| 6,198,394 B1 | 3/2001 | Jacobsen et al. | |
| 6,198,955 B1 * | 3/2001 | Axelgaard et al. | 600/391 |
| 6,208,894 B1 | 3/2001 | Schulman et al. | |
| 6,212,427 B1 | 4/2001 | Hoover | |
| 6,213,942 B1 | 4/2001 | Flach et al. | |
| 6,225,901 B1 | 5/2001 | Kail, IV | |
| 6,245,021 B1 | 6/2001 | Stampfer | |
| 6,259,939 B1 | 7/2001 | Rogel | |
| 6,272,377 B1 | 8/2001 | Sweeney et al. | |
| 6,277,078 B1 | 8/2001 | Porat et al. | |
| 6,287,252 B1 | 9/2001 | Lugo | |
| 6,289,238 B1 | 9/2001 | Besson et al. | |
| 6,290,646 B1 | 9/2001 | Cosentino et al. | |
| 6,295,466 B1 | 9/2001 | Ishikawa et al. | |
| 6,305,943 B1 | 10/2001 | Pougatchev et al. | |
| 6,306,088 B1 | 10/2001 | Krausman et al. | |
| 6,308,094 B1 | 10/2001 | Shusterman et al. | |
| 6,312,378 B1 | 11/2001 | Bardy | |
| 6,315,721 B2 | 11/2001 | Schulman et al. | |
| 6,327,487 B1 | 12/2001 | Stratbucker | |
| 6,336,903 B1 | 1/2002 | Bardy | |
| 6,339,722 B1 | 1/2002 | Heethaar et al. | |
| 6,343,140 B1 | 1/2002 | Brooks | |
| 6,347,245 B1 | 2/2002 | Lee et al. | |
| 6,358,208 B1 | 3/2002 | Lang et al. | |
| 6,385,473 B1 | 5/2002 | Haines et al. | |
| 6,398,727 B1 | 6/2002 | Bui et al. | |
| 6,400,982 B2 | 6/2002 | Sweeney et al. | |
| 6,411,853 B1 | 6/2002 | Millot et al. | |
| 6,416,471 B1 | 7/2002 | Kumar et al. | |
| 6,442,422 B1 | 8/2002 | Duckert | |
| 6,450,820 B1 | 9/2002 | Palsson et al. | |
| 6,450,953 B1 | 9/2002 | Place et al. | |
| 6,453,186 B1 | 9/2002 | Lovejoy et al. | |
| 6,454,707 B1 | 9/2002 | Casscells, III et al. | |
| 6,454,708 B1 | 9/2002 | Ferguson et al. | |
| 6,459,930 B1 | 10/2002 | Takehara et al. | |
| 6,463,328 B1 | 10/2002 | John | |
| 6,473,640 B1 | 10/2002 | Erlebacher | |
| 6,480,733 B1 | 11/2002 | Turcott | |
| 6,480,734 B1 | 11/2002 | Zhang et al. | |
| 6,485,461 B1 | 11/2002 | Mason et al. | |
| 6,490,478 B1 | 12/2002 | Zhang et al. | |
| 6,491,647 B1 | 12/2002 | Bridger et al. | |
| 6,494,829 B1 | 12/2002 | New, Jr. et al. | |
| 6,512,949 B1 | 1/2003 | Combs et al. | |
| 6,520,967 B1 | 2/2003 | Cauthen | |
| 6,527,711 B1 | 3/2003 | Stivoric et al. | |
| 6,527,729 B1 | 3/2003 | Turcott | |
| 6,544,173 B2 | 4/2003 | West et al. | |
| 6,544,174 B2 | 4/2003 | West et al. | |
| 6,546,285 B1 | 4/2003 | Owen et al. | |
| 6,551,251 B2 | 4/2003 | Zuckerwar et al. | |
| 6,551,252 B2 | 4/2003 | Sackner et al. | |
| 6,569,160 B1 | 5/2003 | Goldin et al. | |
| 6,572,557 B2 | 6/2003 | Tchou et al. | |
| 6,572,636 B1 | 6/2003 | Hagen et al. | |
| 6,577,139 B2 | 6/2003 | Cooper | |
| 6,577,893 B1 | 6/2003 | Besson et al. | |
| 6,577,897 B1 | 6/2003 | Shurubura et al. | |
| 6,579,231 B1 | 6/2003 | Phipps | |
| 6,580,942 B1 | 6/2003 | Willshire | |
| 6,584,343 B1 | 6/2003 | Ransbury et al. | |
| 6,587,715 B2 | 7/2003 | Singer | |
| 6,589,170 B1 | 7/2003 | Flach et al. | |
| 6,595,927 B2 | 7/2003 | Pitts-Crick et al. | |
| 6,595,929 B2 | 7/2003 | Stivoric et al. | |
| 6,600,949 B1 | 7/2003 | Turcott | |
| 6,602,201 B1 | 8/2003 | Hepp et al. | |
| 6,605,038 B1 | 8/2003 | Teller et al. | |
| 6,611,705 B2 | 8/2003 | Hopman et al. | |
| 6,611,783 B2 | 8/2003 | Kelly et al. | |
| 6,616,606 B1 | 9/2003 | Petersen et al. | |
| 6,622,042 B1 | 9/2003 | Thacker | |
| 6,636,754 B1 | 10/2003 | Baura et al. | |
| 6,641,542 B2 | 11/2003 | Cho et al. | |
| 6,643,541 B2 | 11/2003 | Mok et al. | |
| 6,645,153 B2 | 11/2003 | Kroll et al. | |
| 6,649,829 B2 | 11/2003 | Garber et al. | |
| 6,650,917 B2 | 11/2003 | Diab et al. | |
| 6,658,300 B2 | 12/2003 | Govari et al. | |
| 6,659,947 B1 | 12/2003 | Carter et al. | |
| 6,659,949 B1 | 12/2003 | Lang et al. | |
| 6,687,540 B2 | 2/2004 | Marcovecchio | |
| 6,697,658 B2 | 2/2004 | Al-Ali | |
| RE38,476 E | 3/2004 | Diab et al. | |
| 6,699,200 B2 | 3/2004 | Cao et al. | |
| 6,701,271 B2 | 3/2004 | Willner et al. | |
| 6,714,813 B2 | 3/2004 | Ishigooka et al. | |
| RE38,492 E | 4/2004 | Diab et al. | |
| 6,721,594 B2 | 4/2004 | Conley et al. | |
| 6,728,572 B2 | 4/2004 | Hsu et al. | |
| 6,748,269 B2 | 6/2004 | Thompson et al. | |
| 6,749,566 B2 | 6/2004 | Russ | |
| 6,751,498 B1 | 6/2004 | Greenberg et al. | |
| 6,760,617 B2 | 7/2004 | Ward et al. | |
| 6,773,396 B2 | 8/2004 | Flach et al. | |
| 6,775,566 B2 | 8/2004 | Nissila | |
| 6,790,178 B1 | 9/2004 | Mault et al. | |
| 6,795,722 B2 | 9/2004 | Sheraton et al. | |
| 6,814,706 B2 | 11/2004 | Barton et al. | |
| 6,816,744 B2 | 11/2004 | Garfield et al. | |
| 6,821,249 B2 | 11/2004 | Casscells, III et al. | |
| 6,824,515 B2 | 11/2004 | Suorsa et al. | |
| 6,827,690 B2 | 12/2004 | Bardy | |
| 6,829,503 B2 | 12/2004 | Alt | |
| 6,858,006 B2 | 2/2005 | MacCarter et al. | |
| 6,871,211 B2 | 3/2005 | Labounty et al. | |
| 6,878,121 B2 | 4/2005 | Krausman et al. | |
| 6,879,850 B2 | 4/2005 | Kimball | |
| 6,881,191 B2 | 4/2005 | Oakley et al. | |
| 6,887,201 B2 | 5/2005 | Bardy | |
| 6,890,096 B2 | 5/2005 | Tokita et al. | |
| 6,893,396 B2 | 5/2005 | Schulze et al. | |
| 6,894,204 B2 | 5/2005 | Dunshee | |
| 6,906,530 B2 | 6/2005 | Geisel | |
| 6,912,414 B2 | 6/2005 | Tong | |
| 6,936,006 B2 | 8/2005 | Sabra | |
| 6,940,403 B2 | 9/2005 | Kail, IV | |
| 6,942,622 B1 | 9/2005 | Turcott | |
| 6,952,695 B1 | 10/2005 | Trinks et al. | |
| 6,970,742 B2 | 11/2005 | Mann et al. | |
| 6,972,683 B2 | 12/2005 | Lestienne et al. | |
| 6,978,177 B1 | 12/2005 | Chen et al. | |
| 6,980,851 B2 | 12/2005 | Zhu et al. | |
| 6,980,852 B2 | 12/2005 | Jersey-Willuhn et al. | |
| 6,985,078 B2 | 1/2006 | Suzuki et al. | |
| 6,987,965 B2 | 1/2006 | Ng et al. | |
| 6,988,989 B2 | 1/2006 | Weiner et al. | |

(56) References Cited

U.S. PATENT DOCUMENTS

| | | |
|---|---|---|
| 6,993,378 B2 | 1/2006 | Wiederhold et al. |
| 6,997,879 B1 | 2/2006 | Turcott |
| 7,003,346 B2 | 2/2006 | Singer |
| 7,018,338 B2 | 3/2006 | Vetter et al. |
| 7,020,508 B2 | 3/2006 | Stivoric et al. |
| 7,027,862 B2 | 4/2006 | Dahl et al. |
| 7,041,062 B2 | 5/2006 | Friedrichs et al. |
| 7,044,911 B2 | 5/2006 | Drinan et al. |
| 7,047,067 B2 | 5/2006 | Gray et al. |
| 7,050,846 B2 | 5/2006 | Sweeney et al. |
| 7,054,679 B2 | 5/2006 | Hirsh |
| 7,059,767 B2 | 6/2006 | Tokita et al. |
| 7,088,242 B2 | 8/2006 | Aupperle et al. |
| 7,113,826 B2 | 9/2006 | Henry et al. |
| 7,118,531 B2 | 10/2006 | Krill |
| 7,127,370 B2 | 10/2006 | Kelly, Jr. et al. |
| 7,129,836 B2 | 10/2006 | Lawson et al. |
| 7,130,396 B2 | 10/2006 | Rogers et al. |
| 7,130,679 B2 | 10/2006 | Parsonnet et al. |
| 7,133,716 B2 | 11/2006 | Kraemer et al. |
| 7,136,697 B2 | 11/2006 | Singer |
| 7,136,703 B1 | 11/2006 | Cappa et al. |
| 7,142,907 B2 | 11/2006 | Xue et al. |
| 7,149,574 B2 | 12/2006 | Yun et al. |
| 7,149,773 B2 | 12/2006 | Haller et al. |
| 7,153,262 B2 | 12/2006 | Stivoric et al. |
| 7,156,807 B2 | 1/2007 | Carter et al. |
| 7,156,808 B2 | 1/2007 | Quy |
| 7,160,252 B2 | 1/2007 | Cho et al. |
| 7,160,253 B2 | 1/2007 | Nissila |
| 7,166,063 B2 | 1/2007 | Rahman et al. |
| 7,167,743 B2 | 1/2007 | Heruth et al. |
| 7,184,821 B2 | 2/2007 | Belalcazar et al. |
| 7,191,000 B2 | 3/2007 | Zhu et al. |
| 7,194,306 B1 | 3/2007 | Turcott |
| 7,206,630 B1 * | 4/2007 | Tarler .................. 600/509 |
| 7,212,849 B2 | 5/2007 | Zhang et al. |
| 7,215,984 B2 | 5/2007 | Diab et al. |
| 7,215,991 B2 | 5/2007 | Besson et al. |
| 7,238,159 B2 | 7/2007 | Banet et al. |
| 7,248,916 B2 | 7/2007 | Bardy |
| 7,251,524 B1 | 7/2007 | Hepp et al. |
| 7,257,438 B2 | 8/2007 | Kinast |
| 7,261,690 B2 | 8/2007 | Teller et al. |
| 7,277,741 B2 | 10/2007 | Debreczeny et al. |
| 7,284,904 B2 | 10/2007 | Tokita et al. |
| 7,285,090 B2 | 10/2007 | Stivoric et al. |
| 7,294,105 B1 | 11/2007 | Islam |
| 7,295,879 B2 | 11/2007 | Denker et al. |
| 7,297,119 B2 | 11/2007 | Westbrook et al. |
| 7,319,386 B2 | 1/2008 | Collins, Jr. et al. |
| 7,336,187 B2 | 2/2008 | Hubbard, Jr. et al. |
| 7,346,380 B2 | 3/2008 | Axelgaard et al. |
| 7,382,247 B2 | 6/2008 | Welch et al. |
| 7,390,299 B2 | 6/2008 | Weiner et al. |
| 7,395,106 B2 | 7/2008 | Ryu et al. |
| 7,423,526 B2 | 9/2008 | Despotis |
| 7,423,537 B2 | 9/2008 | Bonnet et al. |
| 7,443,302 B2 | 10/2008 | Reeder et al. |
| 7,450,024 B2 | 11/2008 | Wildman et al. |
| 7,468,032 B2 | 12/2008 | Stahmann et al. |
| 8,249,686 B2 | 8/2012 | Libbus et al. |
| 8,285,356 B2 | 10/2012 | Bly et al. |
| 2001/0047127 A1 | 11/2001 | New, Jr. et al. |
| 2002/0004640 A1 | 1/2002 | Conn et al. |
| 2002/0019588 A1 | 2/2002 | Marro et al. |
| 2002/0022786 A1 | 2/2002 | Takehara et al. |
| 2002/0028989 A1 | 3/2002 | Pelletier et al. |
| 2002/0032581 A1 | 3/2002 | Reitberg |
| 2002/0045836 A1 | 4/2002 | Alkawwas |
| 2002/0088465 A1 | 7/2002 | Hill |
| 2002/0099277 A1 | 7/2002 | Harry et al. |
| 2002/0116009 A1 | 8/2002 | Fraser et al. |
| 2002/0123672 A1 | 9/2002 | Christophersom et al. |
| 2002/0123674 A1 | 9/2002 | Plicchi et al. |
| 2002/0138017 A1 | 9/2002 | Bui et al. |
| 2002/0167389 A1 | 11/2002 | Uchikoba et al. |
| 2002/0180605 A1 | 12/2002 | Ozguz et al. |
| 2002/0182485 A1 | 12/2002 | Anderson et al. |
| 2003/0023184 A1 | 1/2003 | Pitts-Crick et al. |
| 2003/0028221 A1 | 2/2003 | Zhu et al. |
| 2003/0028327 A1 | 2/2003 | Brunner et al. |
| 2003/0051144 A1 | 3/2003 | Williams |
| 2003/0055460 A1 | 3/2003 | Owen et al. |
| 2003/0069510 A1 | 4/2003 | Semler |
| 2003/0083581 A1 | 5/2003 | Taha et al. |
| 2003/0085717 A1 | 5/2003 | Cooper |
| 2003/0087244 A1 | 5/2003 | McCarthy |
| 2003/0092975 A1 | 5/2003 | Casscells, III et al. |
| 2003/0093125 A1 | 5/2003 | Zhu et al. |
| 2003/0093298 A1 | 5/2003 | Hernandez et al. |
| 2003/0100367 A1 | 5/2003 | Cooke |
| 2003/0135127 A1 | 7/2003 | Sackner et al. |
| 2003/0143544 A1 | 7/2003 | McCarthy |
| 2003/0149349 A1 | 8/2003 | Jensen |
| 2003/0187370 A1 | 10/2003 | Kodama |
| 2003/0191503 A1 | 10/2003 | Zhu et al. |
| 2003/0212319 A1 | 11/2003 | Magill |
| 2003/0221687 A1 | 12/2003 | Kaigler |
| 2003/0233129 A1 | 12/2003 | Matos |
| 2004/0006279 A1 | 1/2004 | Arad (Abboud) |
| 2004/0010303 A1 | 1/2004 | Bolea et al. |
| 2004/0015058 A1 | 1/2004 | Besson et al. |
| 2004/0019292 A1 | 1/2004 | Drinan et al. |
| 2004/0044293 A1 | 3/2004 | Burton |
| 2004/0049132 A1 | 3/2004 | Barron et al. |
| 2004/0073094 A1 | 4/2004 | Baker |
| 2004/0073126 A1 | 4/2004 | Rowlandson |
| 2004/0077954 A1 | 4/2004 | Oakley et al. |
| 2004/0100376 A1 | 5/2004 | Lye et al. |
| 2004/0102683 A1 | 5/2004 | Khanuja et al. |
| 2004/0106951 A1 | 6/2004 | Edman et al. |
| 2004/0127790 A1 | 7/2004 | Lang et al. |
| 2004/0133079 A1 | 7/2004 | Mazar et al. |
| 2004/0133081 A1 | 7/2004 | Teller et al. |
| 2004/0134496 A1 | 7/2004 | Cho et al. |
| 2004/0143170 A1 | 7/2004 | DuRousseau |
| 2004/0147969 A1 | 7/2004 | Mann et al. |
| 2004/0152956 A1 | 8/2004 | Korman |
| 2004/0158132 A1 | 8/2004 | Zaleski |
| 2004/0167389 A1 | 8/2004 | Brabrand |
| 2004/0172080 A1 | 9/2004 | Stadler et al. |
| 2004/0199056 A1 | 10/2004 | Husemann et al. |
| 2004/0215240 A1 | 10/2004 | Lovett et al. |
| 2004/0220639 A1 | 11/2004 | Mulligan et al. |
| 2004/0225199 A1 | 11/2004 | Evanyk et al. |
| 2004/0225203 A1 | 11/2004 | Jemison et al. |
| 2004/0243018 A1 | 12/2004 | Organ et al. |
| 2004/0267142 A1 | 12/2004 | Paul |
| 2005/0004506 A1 | 1/2005 | Gyory |
| 2005/0015094 A1 | 1/2005 | Keller |
| 2005/0015095 A1 | 1/2005 | Keller |
| 2005/0020935 A1 | 1/2005 | Helzel et al. |
| 2005/0027175 A1 | 2/2005 | Yang |
| 2005/0027204 A1 | 2/2005 | Kligfield et al. |
| 2005/0027207 A1 | 2/2005 | Westbrook et al. |
| 2005/0027918 A1 | 2/2005 | Govindarajulu et al. |
| 2005/0043675 A1 | 2/2005 | Pastore et al. |
| 2005/0054944 A1 | 3/2005 | Nakada et al. |
| 2005/0065445 A1 | 3/2005 | Arzbaecher et al. |
| 2005/0065571 A1 | 3/2005 | Imran |
| 2005/0070768 A1 | 3/2005 | Zhu et al. |
| 2005/0070778 A1 | 3/2005 | Lackey et al. |
| 2005/0080346 A1 | 4/2005 | Gianchandani et al. |
| 2005/0080460 A1 | 4/2005 | Wang et al. |
| 2005/0080463 A1 | 4/2005 | Stahmann et al. |
| 2005/0085734 A1 | 4/2005 | Tehrani |
| 2005/0091338 A1 | 4/2005 | de la Huerga |
| 2005/0096513 A1 | 5/2005 | Ozguz et al. |
| 2005/0113703 A1 | 5/2005 | Farringdon et al. |
| 2005/0124878 A1 | 6/2005 | Sharony |
| 2005/0124901 A1 | 6/2005 | Misczynski et al. |
| 2005/0124908 A1 | 6/2005 | Belalcazar et al. |
| 2005/0131288 A1 | 6/2005 | Turner et al. |

(56) References Cited

U.S. PATENT DOCUMENTS

| | | |
|---|---|---|
| 2005/0137464 A1 | 6/2005 | Bomba |
| 2005/0137626 A1 | 6/2005 | Pastore et al. |
| 2005/0148895 A1 | 7/2005 | Misczynski et al. |
| 2005/0158539 A1 | 7/2005 | Murphy et al. |
| 2005/0177038 A1 | 8/2005 | Kolpin et al. |
| 2005/0187482 A1 | 8/2005 | O'Brien et al. |
| 2005/0187796 A1 | 8/2005 | Rosenfeld et al. |
| 2005/0192488 A1 | 9/2005 | Bryenton et al. |
| 2005/0197654 A1 | 9/2005 | Edman et al. |
| 2005/0203433 A1 | 9/2005 | Singer |
| 2005/0203435 A1 | 9/2005 | Nakada |
| 2005/0203637 A1 | 9/2005 | Edman et al. |
| 2005/0206518 A1 | 9/2005 | Welch et al. |
| 2005/0215914 A1 | 9/2005 | Bornzin et al. |
| 2005/0215918 A1 | 9/2005 | Frantz et al. |
| 2005/0228234 A1 | 10/2005 | Yang |
| 2005/0228244 A1 | 10/2005 | Banet |
| 2005/0239493 A1 | 10/2005 | Batkin et al. |
| 2005/0240087 A1 | 10/2005 | Keenan et al. |
| 2005/0251004 A1* | 11/2005 | Istvan et al. .................. 600/395 |
| 2005/0251044 A1 | 11/2005 | Hoctor et al. |
| 2005/0256418 A1 | 11/2005 | Mietus et al. |
| 2005/0261598 A1 | 11/2005 | Banet et al. |
| 2005/0261743 A1 | 11/2005 | Kroll |
| 2005/0267376 A1 | 12/2005 | Marossero et al. |
| 2005/0267377 A1 | 12/2005 | Marossero et al. |
| 2005/0267381 A1 | 12/2005 | Benditt et al. |
| 2005/0273023 A1 | 12/2005 | Bystrom et al. |
| 2005/0277841 A1* | 12/2005 | Shennib ........................ 600/511 |
| 2005/0277842 A1 | 12/2005 | Silva |
| 2005/0277992 A1 | 12/2005 | Koh et al. |
| 2005/0280531 A1 | 12/2005 | Fadem et al. |
| 2005/0283197 A1 | 12/2005 | Daum et al. |
| 2005/0288601 A1 | 12/2005 | Wood et al. |
| 2006/0004300 A1 | 1/2006 | Kennedy |
| 2006/0004377 A1 | 1/2006 | Keller |
| 2006/0009697 A1 | 1/2006 | Banet et al. |
| 2006/0009701 A1 | 1/2006 | Nissila et al. |
| 2006/0010090 A1 | 1/2006 | Brockway et al. |
| 2006/0020218 A1 | 1/2006 | Freeman et al. |
| 2006/0025661 A1 | 2/2006 | Sweeney et al. |
| 2006/0030781 A1 | 2/2006 | Shennib |
| 2006/0030782 A1 | 2/2006 | Shennib |
| 2006/0031102 A1 | 2/2006 | Teller et al. |
| 2006/0041280 A1 | 2/2006 | Stahmann et al. |
| 2006/0047215 A1 | 3/2006 | Newman et al. |
| 2006/0052678 A1 | 3/2006 | Drinan et al. |
| 2006/0058543 A1 | 3/2006 | Walter et al. |
| 2006/0058593 A1 | 3/2006 | Drinan et al. |
| 2006/0064030 A1 | 3/2006 | Cosentino et al. |
| 2006/0064040 A1 | 3/2006 | Berger et al. |
| 2006/0064142 A1 | 3/2006 | Chavan et al. |
| 2006/0066449 A1 | 3/2006 | Johnson |
| 2006/0074283 A1 | 4/2006 | Henderson et al. |
| 2006/0074462 A1 | 4/2006 | Verhoef |
| 2006/0075257 A1 | 4/2006 | Martis et al. |
| 2006/0084881 A1 | 4/2006 | Korzinov et al. |
| 2006/0085049 A1 | 4/2006 | Cory et al. |
| 2006/0089679 A1 | 4/2006 | Zhu et al. |
| 2006/0094948 A1 | 5/2006 | Gough et al. |
| 2006/0102476 A1 | 5/2006 | Niwa et al. |
| 2006/0116592 A1 | 6/2006 | Zhou et al. |
| 2006/0122474 A1 | 6/2006 | Teller et al. |
| 2006/0142654 A1 | 6/2006 | Rytky |
| 2006/0142820 A1 | 6/2006 | Von Arx et al. |
| 2006/0149168 A1 | 7/2006 | Czarnek |
| 2006/0155183 A1 | 7/2006 | Kroecker et al. |
| 2006/0155200 A1 | 7/2006 | Ng |
| 2006/0157893 A1 | 7/2006 | Patel |
| 2006/0161073 A1 | 7/2006 | Singer |
| 2006/0161205 A1 | 7/2006 | Mitrani et al. |
| 2006/0161459 A9 | 7/2006 | Rosenfeld et al. |
| 2006/0167374 A1 | 7/2006 | Takehara et al. |
| 2006/0173257 A1 | 8/2006 | Nagai et al. |
| 2006/0173269 A1 | 8/2006 | Glossop |
| 2006/0195020 A1 | 8/2006 | Martin et al. |
| 2006/0195039 A1 | 8/2006 | Drew et al. |
| 2006/0195097 A1 | 8/2006 | Evans et al. |
| 2006/0195144 A1 | 8/2006 | Giftakis et al. |
| 2006/0202816 A1 | 9/2006 | Crump et al. |
| 2006/0212097 A1 | 9/2006 | Varadan et al. |
| 2006/0224051 A1 | 10/2006 | Teller et al. |
| 2006/0224072 A1* | 10/2006 | Shennib ........................ 600/509 |
| 2006/0224079 A1 | 10/2006 | Washchuk |
| 2006/0235281 A1 | 10/2006 | Tuccillo |
| 2006/0235316 A1 | 10/2006 | Ungless et al. |
| 2006/0235489 A1 | 10/2006 | Drew et al. |
| 2006/0241641 A1 | 10/2006 | Albans et al. |
| 2006/0241701 A1 | 10/2006 | Markowitz et al. |
| 2006/0241722 A1 | 10/2006 | Thacker et al. |
| 2006/0247545 A1 | 11/2006 | St. Martin |
| 2006/0252999 A1 | 11/2006 | Devaul et al. |
| 2006/0253005 A1 | 11/2006 | Drinan et al. |
| 2006/0253044 A1 | 11/2006 | Zhang et al. |
| 2006/0258952 A1 | 11/2006 | Stahmann et al. |
| 2006/0264730 A1 | 11/2006 | Stivoric et al. |
| 2006/0264767 A1 | 11/2006 | Shennib |
| 2006/0264776 A1 | 11/2006 | Stahmann et al. |
| 2006/0271116 A1 | 11/2006 | Stahmann et al. |
| 2006/0276714 A1 | 12/2006 | Holt et al. |
| 2006/0281981 A1 | 12/2006 | Jang et al. |
| 2006/0281996 A1 | 12/2006 | Kuo et al. |
| 2006/0293571 A1 | 12/2006 | Bao et al. |
| 2006/0293609 A1 | 12/2006 | Stahmann et al. |
| 2007/0010721 A1 | 1/2007 | Chen et al. |
| 2007/0010750 A1 | 1/2007 | Ueno et al. |
| 2007/0015973 A1 | 1/2007 | Nanikashvili |
| 2007/0015976 A1 | 1/2007 | Miesel et al. |
| 2007/0016089 A1 | 1/2007 | Fischell et al. |
| 2007/0021678 A1 | 1/2007 | Beck et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027388 A1 | 2/2007 | Chou |
| 2007/0027497 A1 | 2/2007 | Parnis |
| 2007/0038038 A1 | 2/2007 | Stivoric et al. |
| 2007/0038078 A1 | 2/2007 | Osadchy |
| 2007/0038255 A1 | 2/2007 | Kieval et al. |
| 2007/0038262 A1 | 2/2007 | Kieval et al. |
| 2007/0043301 A1 | 2/2007 | Martinsen et al. |
| 2007/0043303 A1 | 2/2007 | Osypka et al. |
| 2007/0048224 A1 | 3/2007 | Howell et al. |
| 2007/0060800 A1 | 3/2007 | Drinan et al. |
| 2007/0060802 A1 | 3/2007 | Ghevondian et al. |
| 2007/0073132 A1 | 3/2007 | Vosch |
| 2007/0073168 A1 | 3/2007 | Zhang et al. |
| 2007/0073181 A1 | 3/2007 | Pu et al. |
| 2007/0073361 A1 | 3/2007 | Goren et al. |
| 2007/0082189 A1 | 4/2007 | Gillette |
| 2007/0083092 A1 | 4/2007 | Rippo et al. |
| 2007/0092862 A1 | 4/2007 | Gerber |
| 2007/0104840 A1 | 5/2007 | Singer |
| 2007/0106132 A1 | 5/2007 | Elhag et al. |
| 2007/0106137 A1 | 5/2007 | Baker, Jr. et al. |
| 2007/0106167 A1 | 5/2007 | Kinast |
| 2007/0118039 A1 | 5/2007 | Bodecker et al. |
| 2007/0123756 A1 | 5/2007 | Kitajima et al. |
| 2007/0123903 A1 | 5/2007 | Raymond et al. |
| 2007/0123904 A1 | 5/2007 | Stad et al. |
| 2007/0129622 A1 | 6/2007 | Bourget et al. |
| 2007/0129643 A1 | 6/2007 | Kwok et al. |
| 2007/0129769 A1 | 6/2007 | Bourget et al. |
| 2007/0142715 A1 | 6/2007 | Banet et al. |
| 2007/0142732 A1 | 6/2007 | Brockway et al. |
| 2007/0149282 A1 | 6/2007 | Lu et al. |
| 2007/0150008 A1 | 6/2007 | Jones et al. |
| 2007/0150009 A1 | 6/2007 | Kveen et al. |
| 2007/0150029 A1 | 6/2007 | Bourget et al. |
| 2007/0162089 A1 | 7/2007 | Mosesov |
| 2007/0167753 A1 | 7/2007 | Van Wyk et al. |

(56) References Cited

U.S. PATENT DOCUMENTS

| | | |
|---|---|---|
| 2007/0167848 A1 | 7/2007 | Kuo et al. |
| 2007/0167849 A1 | 7/2007 | Zhang et al. |
| 2007/0167850 A1 | 7/2007 | Russell et al. |
| 2007/0172424 A1 | 7/2007 | Roser |
| 2007/0173705 A1 | 7/2007 | Teller et al. |
| 2007/0180047 A1 | 8/2007 | Dong et al. |
| 2007/0180140 A1 | 8/2007 | Welch et al. |
| 2007/0191723 A1 | 8/2007 | Prystowsky et al. |
| 2007/0207858 A1 | 9/2007 | Breving |
| 2007/0208233 A1 | 9/2007 | Kovacs |
| 2007/0208235 A1 | 9/2007 | Besson et al. |
| 2007/0208262 A1 | 9/2007 | Kovacs |
| 2007/0232867 A1 | 10/2007 | Hansmann |
| 2007/0249946 A1 | 10/2007 | Kumar et al. |
| 2007/0250121 A1 | 10/2007 | Miesel et al. |
| 2007/0255120 A1 | 11/2007 | Rosnov |
| 2007/0255153 A1 | 11/2007 | Kumar et al. |
| 2007/0255184 A1 | 11/2007 | Shennib |
| 2007/0255531 A1 | 11/2007 | Drew |
| 2007/0260133 A1 | 11/2007 | Meyer |
| 2007/0260155 A1 | 11/2007 | Rapoport et al. |
| 2007/0260289 A1 | 11/2007 | Giftakis et al. |
| 2007/0270678 A1 | 11/2007 | Fadem et al. |
| 2007/0273504 A1 | 11/2007 | Tran |
| 2007/0276273 A1 | 11/2007 | Watson, Jr |
| 2007/0282173 A1 | 12/2007 | Wang et al. |
| 2007/0299325 A1 | 12/2007 | Farrell et al. |
| 2008/0004499 A1 | 1/2008 | Davis |
| 2008/0004904 A1 | 1/2008 | Tran |
| 2008/0024293 A1 | 1/2008 | Stylos |
| 2008/0024294 A1 | 1/2008 | Mazar |
| 2008/0039700 A1 | 2/2008 | Drinan et al. |
| 2008/0058614 A1 | 3/2008 | Banet et al. |
| 2008/0059239 A1 | 3/2008 | Gerst et al. |
| 2008/0091089 A1 | 4/2008 | Guillory et al. |
| 2008/0091090 A1 | 4/2008 | Guillory et al. |
| 2008/0114220 A1 | 5/2008 | Banet et al. |
| 2008/0139934 A1 | 6/2008 | McMorrow et al. |
| 2008/0139953 A1 | 6/2008 | Baker et al. |
| 2008/0146892 A1 | 6/2008 | LeBoeuf et al. |
| 2008/0167538 A1 | 7/2008 | Teller et al. |
| 2008/0171918 A1 | 7/2008 | Teller et al. |
| 2008/0171922 A1 | 7/2008 | Teller et al. |
| 2008/0171929 A1 | 7/2008 | Katims |
| 2008/0183052 A1 | 7/2008 | Teller et al. |
| 2008/0200774 A1 | 8/2008 | Luo |
| 2008/0214903 A1 | 9/2008 | Orbach |
| 2008/0221399 A1 | 9/2008 | Zhou et al. |
| 2008/0221402 A1 | 9/2008 | Despotis |
| 2008/0224852 A1 | 9/2008 | Dicks et al. |
| 2008/0228084 A1 | 9/2008 | Bedard et al. |
| 2008/0287751 A1 | 11/2008 | Stivoric et al. |
| 2008/0287752 A1 | 11/2008 | Stroetz et al. |
| 2008/0287769 A1* | 11/2008 | Kurzweil ............. A61B 5/0408 600/388 |
| 2008/0294019 A1 | 11/2008 | Tran |
| 2008/0294020 A1 | 11/2008 | Sapounas |
| 2008/0318681 A1 | 12/2008 | Rofougaran et al. |
| 2008/0319279 A1 | 12/2008 | Ramsay et al. |
| 2009/0005016 A1 | 1/2009 | Eng et al. |
| 2009/0018410 A1 | 1/2009 | Coene et al. |
| 2009/0018456 A1 | 1/2009 | Hung |
| 2009/0054737 A1 | 2/2009 | Magar et al. |
| 2009/0062670 A1 | 3/2009 | Sterling et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0132018 A1 | 5/2009 | DiUbaldi et al. |
| 2009/0182204 A1 | 7/2009 | Semler et al. |
| 2009/0234410 A1 | 9/2009 | Libbus et al. |
| 2009/0264792 A1 | 10/2009 | Mazar |
| 2009/0292194 A1 | 11/2009 | Libbus et al. |
| 2010/0056881 A1 | 3/2010 | Libbus et al. |
| 2010/0081913 A1 | 4/2010 | Cross et al. |
| 2010/0191310 A1 | 7/2010 | Bly et al. |
| 2011/0245711 A1 | 10/2011 | Katra et al. |
| 2011/0270049 A1 | 11/2011 | Katra et al. |
| 2012/0310070 A1 | 12/2012 | Kumar et al. |

FOREIGN PATENT DOCUMENTS

| | | |
|---|---|---|
| WO | WO 03/082080 A2 | 10/2003 |
| WO | WO 2005/051164 A2 | 6/2005 |
| WO | WO 2005/104930 A1 | 11/2005 |
| WO | WO 2006/008745 A2 | 1/2006 |
| WO | WO 2006/102476 A2 | 9/2006 |
| WO | WO 2006/111878 A1 | 11/2006 |
| WO | WO 2007/041783 A1 | 4/2007 |
| WO | WO 2007/106455 A2 | 9/2007 |

OTHER PUBLICATIONS

3M Corporation, "3M Surgical Tapes—Choose the Correct Tape" quicksheet (2004).

Abraham, "New approaches to monitoring heart failure before symptoms appear," Rev Cardiovasc Med. 2006 ;7 Suppl 1 :33-41.

AD5934: 250 kSPS 12-Bit Impedance Converter Network Analyzer, Analog Devices, Rev. A. Retrieved from the Internet: <<http://www.analog.com/static/imported-files/data_sheets/AD5934.pdf>>, 40 pages. Copyright 2005-2008.

Adams, Jr. "Guiding heart failure care by invasive hemodynamic measurements: possible or useful?", Journal of Cardiac Failure 2002; 8(2):71-73.

Adamson et al., "Continuous autonomic assessment in patients with symptomatic heart failure: prognostic value of heart rate variability measured by an implanted cardiac resynchronization device ," Circulation. 2004;110:2389-2394.

Adamson et al., "Ongoing right ventricular hemodynamics in heart failure," J Am Coll Cardiol, 2003; 41:565-57.

Adamson, "Integrating device monitoring into the infrastructure and workflow of routine practice," Rev Cardiovasc Med. 2006 ;7 Suppl 1:42-6.

Adhere [presentation], "Insights from the Adhere Registry: Data from over 100,000 patient cases," 2005, 70 pages total.

Advamed White Sheet, "Health Information Technology: Improving Patient Safety and Quality of Care," Jun. 2005, 23 pages.

Aghababian, "Acutely decompensated heart failure: opportunities to improve care and outcomes in the emergency department," Rev Cardiovasc Med. 2002;3 Suppl 4:S3-9.

Albert, "Bioimpedance to prevent heart failure hospitalization," Curr Heart Fail Rep. Sep. 2006;3(3):136-42.

American Heart Association, "Heart Disease and Stroke Statistics—2006 Update," 2006, 43 pages.

American Heart Association, "Heart Disease and Stroke Statistics—2007 Update. A Report From the American Heart Association Statistics Committee and Stroke Statistics Subcommittee," Circulation 2007; 115;e69-e171.

Belalcazar et al., "Monitoring lung edema using the pacemaker pulse and skin electrodes," Physiol. Meas. 2005; 26:S153-S163.

Bennet, "Development of implantable devices for continuous ambulatory monitoring of central hemodynamic values in heart failure patients," PACE Jun. 2005; 28:573-584.

Bourge, "Case studies in advanced monitoring with the chronicle device," Rev Cardiovasc Med. 2006 ;7 Suppl 1:S56-61.

(56) References Cited

OTHER PUBLICATIONS

Braunschweig, "Continous haemodynamic monitoring during withdrawal of diuretics in patients with congestive heart failure," European Heart Journal 2002 23(1):59-69.
Braunschweig, "Dynamic changes in right ventricular pressures during haemodialysis recorded with an implantable haemodynamic monitor ," Nephrol Dial Transplant 2006; 21:176-183.
Brennan, "Measuring a Grounded Impedance Profile Using the AD5933," Analog Devices, 2006; retrieved from the Internet <<http://http://www.analog.com/static/imported-files/application_notes/427095282381510189AN847_0.pdf>>, 12 pages total.
Buono et al., "The effect of ambient air temperature on whole-body bioelectrical impedance," Physiol. Meas. 2004;25:119-123.
Burkhoff et al., "Heart failure with a normal ejection fraction: Is it really a disorder of diastolic function?" Circulation 2003; 107:656-658.
Burr et al., "Heart rate variability and 24-hour minimum heart rate," Biological Research for Nursing, 2006; 7(4):256-267.
Cardionet, "CardioNet Mobile Cardiac Outpatient Telemetry: Addendum to Patient Education Guide", CardioNet, Inc., 2007, 2 pages.
Cardionet, "Patient Education Guide", CardioNet, Inc., 2007, 7 pages.
Charach et al., "Transthoracic monitoring of the impedance of the right lung in patients with cardiogenic pulmonary edema," Crit Care Med Jun. 2001;29(6):1137-1144.
Charlson et al., "Can disease management target patients most likely to generate high costs? The Impact of Comorbidity," Journal of General Internal Medicine, Apr. 2007, 22(4):464-469.
Chaudhry et al., "Telemonitoring for patients with chronic heart failure: a systematic review," J Card Fail. Feb. 2007; 13(1): 56-62.
Chung et al., "White coat hypertension: Not so benign after all?," Journal of Human Hypertension (2003) 17, 807-809.
Cleland et al., "The EuroHeart Failure survey programme—a survey on the quality of care among patients with heart failure in Europe—Part 1: patient characteristics and diagnosis," European Heart Journal 2003 24(5):442-463.
Cooley, "The Parameters of Transthoracic Electical Conduction," Annals of the New York Academy of Sciences, 1970; 170(2):702-713.
Cowie et al., "Hospitalization of patients with heart failure. A population-based study," European Heart Journal 2002 23(11):877-885.
Dimri, Chapter 1: Fractals in geophysics and seimology: an introduction, Fractal Behaviour of the Earth System, Springer Berlin Heidelberg 2005, pp. 1-22. [Summary and 1st page Only].
El-Dawlatly et al., "Impedance cardiography: noninvasive assessment of hemodynamics and thoracic fluid content during bariatric surgery," Obesity Surgery, May 2005, 15(5):655-658.
EM Microelectronic—Marin SA, "Plastic Flexible LCD," [product brochure]; retrieved from the Internet: <<http://www.em-microelectronic.com/Line.asp?IdLine=48>>, copyright 2009, 2 pages total.
Erdmann, "Editorials: The value of diuretics in chronic heart failure demonstrated by an implanted haemodynamic monitor," European Heart Journal 2002 23(1):7-9.
FDA—Medtronic Chronicle Implantable Hemodynamic Monitoring System P050032: Panel Package Section 11: Chronicle IHM Summary of Safety and Effectiveness, 2007; retrieved from the Internet: <http://www.fda.gov/OHRMS/DOCKETS/AC/07/briefing/2007-4284b1_04.pdf>, 77 pages total.
FDA—Medtronic Inc., Chronicle 9520B Implantable Hemodynamic Monitor Reference Manual, 2007, 112 pages.
FDA Executive Summary Memorandum, prepared for Mar. 1, 2007 meeting of the Circulatory Systems Devices Advisory Panel, P050032 Medtronic, Inc. Chronicle Implantable Hemodynamic Monitor (IHM) System, 23 pages. Retrieved from the Internet: <<http://www.fda.gov/ohrms/dockets/ac/07/briefing/2007-4284b1_02.pdf>>.
FDA Executive Summary, Medtronic Chronicle Implantable Hemodynamic Monitoring System P050032: Panel Package Sponsor Executive Summary; vol. 1, section 4: Executive Summary. 2007, 12 pages total. Retrieved from the Internet: <<http://www.fda.gov/OHRMS/DOCKETS/AC/07/briefing/2007-4284b1_03.pdf>>.
FDA, Draft questions for Chronicle Advisory Panel Meeting, 2007, 3 pages total. Retrieved from the Internet: <<http://www.fda.gov/ohrms/dockets/ac/07/questions/2007-4284q1_draft.pdf>>.
FDA, References for Mar. 1 Circulatory System Devices Panel, 2007, 1 page total. Retrieved from the Internet: <<http://www.fda.gov/OHRMS/DOCKETS/AC/07/briefing/2007-4284bib1_01.pdf>>.
Fonarow et al., "Risk stratification for in-hospital mortality in acutely decompensated heart failure: classification and regression tree analysis," JAMA. Feb. 2, 2005;293(5):572-580.
Fonarow, "How well are chronic heart failure patients being managed?", Rev Cardiovasc Med. 2006;7 Suppl 1:S3-11.
Fonarow, "Maximizing Heart Failure Care: Opportunities to Improve Patient Outcomes" [Powerpoint Presentation], A CME National Faculty Program, downloaded from the Internet <<http://www.medreviews.com/media/MaxHFCore.ppt>>, 130 pages total.
Fonarow, "Proactive monitoring and management of the chronic heart failure patient," Rev Cardiovasc Med. 2006; 7 Suppl 1:S1-2.
Fonarow, "The Acute Decompensated Heart Failure National Registry (ADHERE): opportunities to improve care of patients hospitalized with acute decompensated heart failure," Rev Cardiovasc Med. 2003;4 Suppl 7:S21-S30.
Ganion et al., "Intrathoracic impedance to monitor heart failure status: a comparison of two methods in a chronic heart failure dog model," Congest Heart Fail. Jul.-Aug. 2005;11(4):177-81, 211.
Gass et al., "Critical pathways in the management of acute decompensated heart failure: A CME-Accredited Accredited monograph," Mount Sinai School of Medicine, 2004, 32 pages total.
Gheorghiade et al., "Congestion is an important diagnostic and therapeutic target in heart failure," Rev Cardiovasc Med. 2006 ;7 Suppl 1 :12-24.
Gilliam, III et al., "Changes in heart rate variability, quality of life, and activity in cardiac resynchronization therapy patients: results of the HF-HRV registry," Pacing and Clinical Electrophysiology, Jan. 18, 2007; 30(1): 56-64.
Gilliam, III et al., "Prognostic value of heart rate variability footprint and standard deviation of average 5-minute intrinsic R-R intervals for mortality in cardiac resynchronization therapy patients.," J Electrocardiol. Oct. 2007;40(4):336-42.
Gniadecka, "Localization of dermal edema in lipodermatosclerosis, lymphedema, and cardiac insufficiency high-frequency ultrasound examination of intradermal echogenicity," J Am Acad oDermatol, Jul. 1996; 35(1):37-41.
Goldberg et al., "Randomized trial of a daily electronic home monitoring system in patients with advanced heart failure: The Weight Monitoring in Heart Failure (WHARF) Trial," American Heart Journal, Oct. 2003; 416(4):705-712.
Grap et al., "Actigraphy in the Critically Ill: Correlation With Activity, Agitation, and Sedation," American Journal of Critical Care. 2005;14: 52-60.
Gudivaka et al., "Single- and multifrequency models for bioelectrical impedance analysis of body water compartments," J Appl Physiol, 1999;87(3):1087-1096.
Guyton et al., Unit V: The Body Fluids and Kidneys, Chapter 25: The Body Fluid Compartments: Extracellular and Intracellular Fluids; Interstitial Fluid and Edema, Guyton & Hall Textbook of Medical Physiology 11th Edition, Saunders 2005; pp. 291-306.
Hadase et al., "Very low frequency power of heart rate variability is a powerful predictor of clinical prognosis in patients with congestive heart Failure," Circ J 2004; 68(4):343-347.
Hallstrom et al., "Structural relationships between measures based on heart beat intervals: potential for improved risk assessment," IEEE Biomedical Engineering 2004, 51(8):1414-1420.
HFSA 2006 Comprehensive Heart Failure Practice Guideline—Executive Summary: HFSA 2006 Comprehensive Heart Failure Practice Guideline, Journal of Cardiac Failure 2006;12(1):10-e38.

(56) References Cited

OTHER PUBLICATIONS

HFSA 2006 Comprehensive Heart Failure Practice Guideline—Section 12: Evaluation and Management of Patients With Acute Decompensated Heart Failure, Journal of Cardiac Failure 2006;12(1):e86-e103.
HFSA 2006 Comprehensive Heart Failure Practice Guideline—Section 2: Conceptualization and Working Definition of Heart Failure, Journal of Cardiac Failure 2006;12(1):e10-e11.
HFSA 2006 Comprehensive Heart Failure Practice Guideline—Section 3: Prevention of Ventricular Remodeling Cardiac Dysfunction, and Heart Failure Overview, Journal of Cardiac Failure 2006;12(1):e12-e15.
HFSA 2006 Comprehensive Heart Failure Practice Guideline—Section 4: Evaluation of Patients for Ventricular Dysfunction and Heart Failure, Journal of Cardiac Failure 2006;12(1):e16-e25.
HFSA 2006 Comprehensive Heart Failure Practice Guideline—Section 8: Disease Management in Heart Failure Education and Counseling, Journal of Cardiac Failure 2006;12(1):e58-e68.
HRV Enterprises, LLC, "Heart Rate Variability Seminars," downloaded from the Internet: <<http://hrventerprise.com/>> on Apr. 24, 2008, 3 pages total.
HRV Enterprises, LLC, "LoggerPro HRV Biosignal Analysis," downloaded from the Internet: <<http://hrventerprise.com/products.html on Apr. 24, 2008, 3 pages total.
Hunt et al., "ACC/AHA 2005 Guideline Update for the Diagnosis and Management of Chronic Heart Failure in the Adult: A Report of the American College of Cardiology/American Heart Association Task Force on Practice Guidelines (Writing Committee to Update the 2001 Guidelines for the Evaluation and Management of Heart Failure): Developed in Collaboration With the American College of Chest Physicians and the International Society for Heart and Lung Transplantation: Endorsed by the Heart Rhythm Society," Circulation. 2005;112:e154-e235.
Hunt et al., ACC/AHA Guidelines for the Evaluation and Management of Chronic Heart Failure in the Adult: Executive Summary A Report of the American College of Cardiology/American Heart Association Task Force on Practice Guidelines (Committee to Revise the 1995 Guidelines for the Evaluation and Management of Heart Failure), Circulation. 2001;104:2996-3007.
Imhoff et al., "Noninvasive whole-body electrical bioimpedance cardiac output and invasive thermodilution cardiac output in high-risk surgical patients," Critical Care Medicine 2000; 28(8):2812-2818.
Jaeger et al., "Evidence for Increased Intrathoracic Fluid Volume in Man at High Altitude," J Appl Physiol 1979; 47(6): 670-676.
Jaio et al., "Variance fractal dimension analysis of seismic refraction signals," WESCANEX 97: Communications, Power and Computing. IEEE Conference Proceedings., May 22-23, 1997, pp. 163-167 [Abstract Only].
Jerant et al., "Reducing the cost of frequent hospital admissions for congestive heart failure: a randomized trial of a home telecare intervention," Medical Care 2001, 39(11):1234-1245.
Kasper et al., "A randomized trial of the efficacy of multidisciplinary care in heart failure outpatients at high risk of hospital readmission," J Am Coll Cardiol, 2002; 39:471-480.
Kaukinen, "Cardiac output measurement after coronary artery bypass grafting using bolus thermodilution, continuous thermodilution, and whole-body impedance cardiography," Journal of Cardiothoracic and Vascular Anesthesia 2003; 17(2):199-203.
Kawaguchi et al., "Combined ventricular systolic and arterial stiffening in patients with heart failure and preserved ejection fraction: implications for systolic and diastolic reserve limitations," Circulation. 2003;107:714-720.
Kawasaki et al., "Heart rate turbulence and clinical prognosis in hypertrophic cardiomyopathy and myocardial infarction," Circ J. Jul. 2003;67(7):601-604.
Kearney et al., "Predicting death due to progressive heart failure in patients with mild-to-moderate chronic heart failure," J Am Coll Cardiol, 2002; 40(10):1801-1808.

Kitzman et al., "Pathophysiological characterization of isolated diastolic heart failure in comparison to systolic heart failure," JAMA Nov. 2002; 288(17):2144-2150.
Kööbi et al., "Non-invasive measurement of cardiac output: whole-body impedance cardiography in simultaneous comparison with thermodilution and direct oxygen Fick methods," Intensive Care Medicine 1997; 23(11):1132-1137.
Koyama et al., "Evaluation of heart-rate turbulence as a new prognostic marker in patients with chronic heart failure," Circ J 2002; 66(10):902-907.
Krumholz et al., "Predictors of readmission among elderly survivors of admission with heart failure," American Heart Journal 2000; 139(1):72-77.
Kyle et al., "Bioelectrical Impedance Analysis—part I: review of principles and methods," Clin Nutr. Oct. 2004;23(5):1226-1243.
Kyle et al., "Bioelectrical Impedance Analysis—part II: utilization in clinical practice," Clin Nutr. Oct. 2004; 23(5):1430-1453.
Lee et al., "Predicting mortality among patients hospitalized for heart failure: derivation and validation of a clinical model," JAMA 2003;290(19):2581-2587.
Leier "The Physical Examination in Heart Failure—Part I," Congest Heart Fail. Jan.-Feb. 2007;13(1):41-47.
LifeShirt® Model 200 Directions for Use, "Introduction", VivoMetrics, Inc. 9 page total.
Liu et al., "Fractal analysis with applications to seismological pattern recognition of underground nuclear explosions," Singal Processing, Sep. 2000, 80(9):1849-1861. [Abstract Only].
Lozano-Nieto, "Impedance ratio in bioelectrical impedance measurements for body fluid shift determination," Proceedings of the IEEE 24th Annual Northeast Bioengineering Conference, Apr. 9-10, 1998, pp. 24-25.
Lucreziotti et al., "Five-minute recording of heart rate variability in severe chronic heart failure : Correlates with right ventricular function and prognostic implications," American Heart Journal 2000; 139(6):1088-1095.
Lüthje et al., "Detection of heart failure decompensation using intrathoracic impedance monitoring by a triple-chamber implantable defibrillator," Heart Rhythm Sep. 2005;2(9):997-999.
Magalski et al., "Continuous ambulatory right heart pressure measurements with an implantable hemodynamic monitor: a multi-center, 12-Month Follow-up Study of Patients With Chronic Heart Failure," J Card Fail 2002, 8(2):63-70.
Mahlberg et al., "Actigraphy in agitated patients with dementia: Monitoring treatment outcomes," Zeitschrift für Gerontologie and Geriatrie, Jun. 2007; 40(3)178-184. [Abstract Only].
Matthie et al., "Analytic assessment of the various bioimpedance methods used to estimate body water," Appl Physiol 1998; 84(5):1801-1816.
Matthie, "Second generation mixture theory equation for estimating intracellular water using bioimpedance spectroscopy," J Appl Physiol 2005; 99:780-781.
McMurray et al., "Heart Failure: Epidemiology, Aetiology, and Prognosis of Heart Failure," Heart 2000;83:596-602.
Miller, "Home monitoring for congestive heart failure patients," Caring Magazine, Aug. 1995: 53-54.
Moser et al., "Improving outcomes in heart failure: it's not unusual beyond usual Care," Circulation. 2002;105:2810-2812.
Nagels et al., "Actigraphic measurement of agitated behaviour in dementia," International journal of geriatric psychiatry , 2009; 21(4):388-393. [Abstract Only].
Nakamura et al., "Universal scaling law in human behavioral organization," Physical Review Letters, Sep. 28, 2007; 99(13):138103 (4 pages).
Nakaya, "Fractal properties of seismicity in regions affected by large, shallow earthquakes in western Japan: Implications for fault formation processes based on a binary fractal fracture network model," Journal of geophysical research, Jan. 2005; 11(B1):B01310.1-B01310.15. [Abstract Only].
Naylor et al., "Comprehensive discharge planning for the hospitalized elderly: a randomized clinical trial ," Amer. College Physicians 1994; 120(12):999-1006.
Nesiritide (Natrecor) [Presentation] Acutely Decompensated Congestive Heart Failure: Burden of Disease, downloaded from the

(56) References Cited

OTHER PUBLICATIONS

Internet: <<http://www.huntsvillehospital.org/foundation/events/cardiologyupdate/CHF.ppt.>>, 39 pages.
Nieminen et al., "EuroHeart Failure Survey II (EHFS II): a survey on hospitalized acute heart failure patients: description of population," European Heart Journal 2006; 27(22):2725-2736.
Nijsen et al., "The potential value of three-dimensional accelerometry for detection of motor seizures in severe epilepsy," Epilepsy Behav. Aug. 2005;7(1):74-84.
Noble et al., "Diuretic induced change in lung water assessed by electrical impedance tomography," Physiol. Meas. 2000; 21(1):155-163.
Noble et al., "Monitoring patients with left ventricular failure by electrical impedance tomography," Eur J Heart Fail. Dec. 1999;1(4):379-84.
O'Connell et al., "Economic impact of heart failure in the United States: time for a different approach," J Heart Lung Transplant., Jul.-Aug. 1994 ; 13(4):S107-S112.
Ohlsson et al., "Central hemodynamic responses during serial exercise tests in heart failure patients using implantable hemodynamic monitors," Eur J Heart Fail. Jun. 2003;5(3):253-259.
Ohlsson et al., "Continuous ambulatory monitoring of absolute right ventricular pressure and mixed venous oxygen saturation in patients with heart failure using an implantable haemodynamic monitor," European Heart Journal 2001 22(11):942-954.
Packer et al., "Utility of impedance cardiography for the identification of short-term risk of clinical decompensation in stable patients with chronic heart failure," J Am Coll Cardiol, 2006; 47(11):2245-2252.
Palatini et al., "Predictive value of clinic and ambulatory heart rate for mortality in elderly subjects with systolic hypertension" Arch Intern Med. 2002;162:2313-2321.
Piiria et al., "Crackles in patients with fibrosing alveolitis bronchiectasis, COPD, and Heart Failure," Chest May 1991; 99(5):1076-1083.
Pocock et al., "Predictors of mortality in patients with chronic heart failure," Eur Heart J 2006; (27): 65-75.
Poole-Wilson, "Importance of control of fluid volumes in heart failure," European Heart Journal 2000; 22(11):893-894.
Raj et al., 'Letter Regarding Article by Adamson et al, "Continuous Autonomic Assessment in Patients With Symptomatic Heart Failure: Prognostic Value of Heart Rate Variability Measured by an Implanted Cardiac Resynchronization Device"', Circulation 2005;112:e37-e38.
Ramirez et al., "Prognostic value of hemodynamic findings from impedance cardiography in hypertensive stroke," AJH 2005; 18(20):65-72.
Rich et al., "A multidisciplinary intervention to prevent the readmission of elderly patients with congestive heart failure," New Engl. J. Med. 1995;333:1190-1195.
Roglieri et al., "Disease management interventions to improve outcomes in congestive heart failure," Am J Manag Care. Dec. 1997;3(12):1831-1839.
Sahalos et al., "The Electrical impedance of the human thorax as a guide in evaluation of intrathoracic fluid volume," Phys. Med. Biol. 1986; 31:425-439.
Saxon et al., "Remote active monitoring in patients with heart failure (rapid-rf): design and rationale," Journal of Cardiac Failure 2007; 13(4):241-246.
Scharf et al., "Direct digital capture of pulse oximetry waveforms," Proceedings of the Twelfth Southern Biomedical Engineering Conference, 1993., pp. 230-232.
Shabetai, "Monitoring heart failure hemodynamics with an implanted device: its potential to improve outcome," J Am Coll Cardiol, 2003; 41:572-573.
Small, "Integrating monitoring into the Infrastructure and Workflow of Routine Practice: OptiVol," Rev Cardiovasc Med. 2006 ;7 Supp 1: S47-S55.

Smith et al., "Outcomes in heart failure patients with preserved ejection fraction: mortality, readmission, and functional decline ," J Am Coll Cardiol, 2003; 41:1510-1518.
Something in the way he moves, The Economist, 2007, retrieved from the Internet: <<http://www.economist.com/science/printerFriendly.cfm?story id=9861412>>.
Starling, "Improving care of chronic heart failure: advances from drugs to devices," Cleveland Clinic Journal of Medicine Feb. 2003; 70(2):141-146.
Steijaert et al., "The use of multi-frequency impedance to determine total body water and extracellular water in obese and lean female individuals," International Journal of Obesity Oct. 1997; 21(10):930-934.
Stewart et al., "Effects of a home-based intervention among patients with congestive heart failure discharged from acute hospital care," Arch Intern Med. 1998;158:1067-1072.
Stewart et al., "Effects of a multidisciplinary, home-based intervention on planned readmissions and survival among patients with chronic congestive heart failure: a randomised controlled study," The Lancet Sep. 1999, 354(9184):1077-1083.
Stewart et al., "Home-based intervention in congestive heart failure: long-term implications on readmission and survival," Circulation. 2002;105:2861-2866.
Stewart et al., "Prolonged beneficial effects of a home-based intervention on unplanned readmissions and mortality among patients with congestive heart failure," Arch Intern Med. 1999;159:257-261.
Stewart et al., "Trends in Hospitalization for Heart Failure in Scotland, 1990-1996. An Epidemic that has Reached Its Peak?," European Heart Journal 2001 22(3):209-217.
Swedberg et al., "Guidelines for the diagnosis and treatment of chronic heart failure: executive summary (update 2005): The Task Force for the Diagnosis and Treatment of Chronic Heart Failure of the European Society of Cardiology," Eur Heart J. Jun. 2005; 26(11):1115-1140.
Tang, "Case studies in advanced monitoring: OptiVol," Rev Cardiovasc Med. 2006;7 Suppl 1:S62-S66.
The ESCAPE Investigators and ESCAPE Study Coordinators, "Evaluation Study of Congestive Heart Failure and Pulmonary Artery Catheterization Effectiveness," JAMA 2005;294:1625-1633.
Tosi et al., "Seismic signal detection by fractal dimension analysis ," Bulletin of the Seismological Society of America; Aug. 1999; 89(4):970-977. [Abstract Only].
Van De Water et al., "Monitoring the chest with impedance," Chest. 1973;64:597-603.
Van Someren, "Actigraphic monitoring of movement and rest-activity rhythms inaging, Alzheimer's disease, and Parkinson's disease," IEEE Transactions on Rehabilitation Engineering, Dec. 1997; 5(4):394-398. [Abstract Only].
Vasan et al., "Congestive heart failure in subjects with normal versus reduced left ventricular ejection fraction," J Am Coll Cardiol, 1999; 33:1948-1955.
Verdecchia et al., "Adverse prognostic value of a blunted circadian rhythm of heart rate in essential hypertension," Journal of Hypertension 1998; 16(9):1335-1343.
Verdecchia et al., "Ambulatory pulse pressure: a potent predictor of total cardiovascular risk in hypertension," Hypertension. 1998;32:983-988.
Vollmann et al., "Clinical utility of intrathoracic impedance monitoring to alert patients with an implanted device of deteriorating chronic heart failure," Euorpean Heart Journal Advance Access published on Feb. 19, 2007, downloaded from the Internet:<<http://eurheartj.oxfordjournals.org/cgi/content/full/ehl506v1>>, 6 pages total.
Vuksanovic et al., "Effect of posture on heart rate variability spectral measures in children and young adults with heart disease," International Journal of Cardiology 2005;101(2): 273-278.
Wang et al., "Feasibility of using an implantable system to measure thoracic congestion in an ambulatory chronic heart failure canine model," PACE 2005;28(5):404-411.
Wickemeyer et al., #197—"Association between atrial and ventricular tachyarrhythmias, intrathoracic impedance and heart failure decompensation in CRT-D Patients," Journal of Cardiac Failure 2007; 13 (6) Suppl.; S131-132.

(56) References Cited

OTHER PUBLICATIONS

Williams et al, "How do different indicators of cardiac pump function impact upon the long-term prognosis of patients with chronic heart failure," American Heart Journal, 150(5):983.e1-983.e6.

Wonisch et al., "Continuous haemodynamic monitoring during exercise in patients with pulmonary hypertension," Int J Cardiol. Jun. 8, 2005;101(3):415-420.

Wynne et al., "Impedance cardiography: a potential monitor for hemodialysis," Journal of Surgical Research 2006, 133(1):55-60.

Yancy "Current approaches to monitoring and management of heart failure," Rev Cardiovasc Med 2006; 7 Suppl 1:S25-32.

Ypenburg et al., "Intrathoracic Impedance Monitoring to Predict Decompensated Heart Failure," Am J Cardiol 2007, 99(4):554-557.

Yu et al., "Intrathoracic Impedance Monitoring in Patients With Heart Failure: Correlation With Fluid Status and Feasibility of Early Warning Preceding Hospitalization," Circulation. 2005;112:841-848.

Zannad et al., "Incidence, clinical and etiologic features, and outcomes of advanced chronic heart failure: The EPICAL Study," J Am Coll Cardiol, 1999; 33(3):734-742.

Zile, "Heart failure with preserved ejection fraction: is this diastolic heart failure?" J Am Coll Cardiol, 2003; 41(9):1519-1522.

Scapa Medical product listing and descriptions (2008) available at http://www.caapana.com/productlist.jsp and http://www.metplus.co.rs/pdf/prospekti/Samolepljivemedicinsketrake.pdf; retrieved via WayBack Machine Aug. 29, 2013.

\* cited by examiner

BODY ADHERENT PATCH WITH ELECTRONICS FOR PHYSIOLOGIC MONITORING

This application claims priority from provisional U.S. Patent Application No. 61/286,075, titled "Body Adherent Patch with Electronics for Physiologic Monitoring" and filed Dec. 14, 2009, the entire disclosure of which is hereby incorporated by reference herein for all purposes.

BACKGROUND OF THE INVENTION

1. Field of the Invention

The present invention relates to physiologic monitoring and/or therapy. Although embodiments make specific reference to monitoring impedance and electrocardiogram signals with an adherent device, the system methods and devices described herein may be applicable to many applications in which physiological monitoring and/or therapy is used for extended periods, for example wireless physiological monitoring for extended periods.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital. One example of a device to provide long term monitoring of a patient is the Holter monitor, or ambulatory electrocardiography device.

In addition to measuring heart signals with electrocardiograms, known physiologic measurements include impedance measurements. For example, transthoracic impedance measurements can be used to measure hydration and respiration. Although transthoracic measurements can be useful, such measurements may use electrodes that are positioned across the midline of the patient, and may be somewhat uncomfortable and/or cumbersome for the patient to wear. In at least some instances, the electrodes that are held against the skin of the patient may become detached and/or dehydrated, such that the electrodes must be replaced, thereby making long term monitoring more difficult.

Work in relation to embodiments of the present invention suggests that known methods and apparatus for long term monitoring of patients may be less than ideal. In at least some instances, devices that are worn by the patient may be somewhat uncomfortable. Although devices that adhere measurement electrodes and measurement circuitry to the skin with an adhesive can provide improved comfort, work in relation to embodiments of the present invention suggests that the adhesive of such devices can detach from the skin of the patient sooner than would be ideal. These limitations of current devices may lead to patients not wearing the devices as long as would be ideal and not complying with direction from the health care provider in at least some instances, such that data collected may be less than ideal.

Similar difficulties may arise in the monitoring of other subjects, such as persons in non-medical settings, or in the monitoring of animals such as veterinary, agricultural, or wild animal monitoring. Therefore, a need exists for improved subject monitoring. Ideally, such improved subject monitoring would avoid at least some of the shortcomings of the present methods and devices. Ideally, such improved devices will allow an adherent device to be adhered to the skin of the subject with an adhesive so as to carry associated electronics comfortably with the skin of the subject for an extended period.

2. Description of the Background Art

The following U.S. Patents and Publications may describe relevant background art: U.S. Pat. Nos. 3,170,459; 3,805,769; 3,845,757; 3,972,329; 4,141,366; 4,522,211; 4,669,480; 4,838,273; 5,133,355; 5,150,708; 5,450,845; 5,511,533; 5,607,454; 6,141,575; 6,198,955; 6,327,487; 6,795,722; 7,395,106; 2004/0006279; 2004/0015058; 2006/0264730; 2007/0106132; 2007/0208262; 2007/0249946; 2007/0255184; 2008/0171929; 2007/0276273; and 2009/0182204.

BRIEF SUMMARY OF THE INVENTION

In many embodiments, an adherent device to adhere to a skin of a subject comprises a stretchable base layer having an upper side and a lower side and an adhesive coating on the lower side to adhere the base layer to the skin of the subject. The base layer has at least two openings extending therethrough, each of the at least two openings having a size. The adherent device also comprises a stretchable covering layer positioned above and adhered to the base layer with an adhesive to define at least two pockets, and at least two gels, each gel having a size larger than the size of the at least two openings to retain said gel substantially within said pocket. The adherent device further comprises a circuit carrier supported with the stretchable base layer to measure at least one physiologic signal of the subject. The subject may comprise a person, an athlete, a patient, or an animal such as a domesticated or a wild animal.

According to some embodiments, an adherent device to monitor a subject having a skin comprises a stretchable base layer having an upper side and a lower side and an adhesive coating disposed on the lower side to adhere the base layer to the skin of the subject. The base layer has at least two openings extending therethrough, each opening having a size. The adherent device further includes a flexible circuit support having at least two electrodes disposed thereon, each electrode positioned with a respective one of the at least two openings to couple to the skin of the subject. At least two gels are positioned with the at least two openings in the base layer, each gel having a size larger than the size of said each opening. The device also includes a stretchable covering layer positioned above the at least two gels and adhered to the base layer, such that each gel is constrained substantially within a corresponding pocket disposed between the base layer and the covering layer. The adherent device further includes a circuit carrier holding electronic components electrically connected to the at least one electrode with the flexible circuit support to measure at least one physiologic signal of the subject.

In some embodiments, each of the gels and each of the pockets is sized larger than a corresponding opening of the stretchable base layer to retain said gel in said pocket when the stretchable base layer is adhered to the skin of the subject. In some embodiments, the stretchable base layer comprises a thin, flexible, stretchable base layer to stretch with the skin of the subject and conform to folds of the skin of the subject. In some embodiments, the stretchable covering layer comprises a thin, flexible, stretchable covering layer to stretch with the skin of the subject and conform to folds of the skin of the subject. The adherent device may further include a thin, flexible, stretchable overlayer disposed above and adhered to the covering layer. The overlayer may be made of woven fabric.

In some embodiments, the adherent device further comprises a stiffening structure disposed over and coupled to a common perimeter of the base and covering layers and configured to stiffen the perimeter edges of the base and covering layers. The stiffening structure may be configured to be removable after the adherent device is adhered to the subject. In some embodiments, the adherent device further comprises a thin, flexible, stretchable overlayer disposed above and adhered to the covering layer, and the stiffening structure is disposed over and coupled to a common perimeter of the base and covering layers and the overlayer, and the stiffening structure is configured to stiffen the perimeter edges of the base and covering layers and the overlayer. The adherent device according to these embodiments may further include a soft, flexible cover disposed over the circuit carrier and coupled at a common perimeter to the base and covering layers. The cover may comprise a material configured to inhibit liquids from reaching the electronic components. A perimeter of the cover may be disposed under the stiffening structure. In some embodiments, the flexible circuit is configured to be stretchable.

In some embodiments, the flexible circuit is formed of a substantially non-stretchable material, and is geometrically configured to be stretchable. In some embodiments, the flexible circuit comprises a polyester base and traces formed of silver conductive ink. The flexible circuit may comprise a serpentine shape. The flexible circuit may be disposed between the base layer and the covering layer.

In some embodiments, the adherent device further comprises a compliant connection between the circuit carrier and the base layer. In some embodiments, the combination of the base layer and the covering layer is breathable. The combination of the base layer and the covering layer may have a moisture vapor transmission rate of at least 100 g/m$^2$/day.

According to some embodiments, an adherent device comprises a thin, flexible, stretchable base layer having an upper side and a lower side and an adhesive coating on the lower side. At least one electrode is affixed to the base layer and is capable of electrically coupling to the skin of a subject. A flexible circuit is connected to the at least one electrode, and a circuit carrier holding electronic components is electrically connected to the at least one electrode via the flexible circuit and configured to measure at least one physiologic signal of the subject. The adherent device further includes a stiffening structure disposed over and coupled to a perimeter of the base layer and configured to stiffen the perimeter edge of the base layer. In some embodiments, the stiffening structure is configured to be removable when the adherent device is adhered to the subject. The stiffening structure may be made from a vinyl sheet.

In some embodiments, the adherent device further comprises a thin, flexible, stretchable overlayer disposed above and adhered to the base layer, and the stiffening structure is disposed over and coupled to a common perimeter of the base layer and overlayer and is configured to stiffen the perimeter edge of the base layer and overlayer. According to some embodiments, the adherent device further includes a gel patch under each electrode, and each gel patch enhances electrical conductivity between its respective electrode and the skin of the subject. The flexible circuit is configured to be stretchable.

In some embodiments, the adherent device further comprises a soft, flexible cover disposed over the circuit carrier and coupled at a perimeter to the base layer. The cover may comprise a material configured to inhibit liquids from reaching the electronic components. The lower side of the base layer is configured to adhere to the skin of a subject.

In some embodiments, the adherent device further comprises a thin, flexible, stretchable underlayer adhered to the lower side of the base layer, the underlayer configured to adhere to the skin of the subject. The combination of the base layer and underlayer may be breathable. The combination of the base layer and underlayer may has a moisture vapor transmission rate of at least 100 g/m$^2$/day.

In some embodiments, the adherent device further comprises a gel patch under each electrode, and each gel patch enhances electrical conductivity between its respective electrode and the skin of the subject, and a perimeter of each gel patch is sandwiched between the base layer and the underlayer. In some embodiments, the underlayer comprises at least one opening through which electrical contact is made between the at least one electrode and the skin of the subject. The adherent device many further include a compliant connection between the circuit carrier and the base layer.

According to some embodiments, an adherent device comprises a thin, flexible, stretchable base layer having an upper side and a lower side and an adhesive coating on the lower side. At least one electrode is affixed to the base layer and capable of electrically coupling to the skin of a subject. A flexible circuit is connected to the at least one electrode, and is configured to stretch. The adherent device further includes a circuit carrier holding electronic components electrically connected to the at least one electrode via the flexible circuit and configured to measure at least one physiologic signal of the subject.

In some embodiments, the flexible circuit is formed of a substantially non-stretchable material, and is geometrically configured to be stretchable. In some embodiments, the flexible circuit comprises a polyester base and traces formed of silver conductive ink. The flexible circuit may comprise a serpentine shape. The flexible circuit may comprise a sawtooth shape.

In some embodiments, the adherent device further comprises gel patch under each electrode, and each gel patch enhances electrical conductivity between its respective electrode and the skin of the subject. In some embodiments, the base layer is configured to adhere to the skin of the subject, and the adherent device further comprises a thin, flexible, stretchable overlayer disposed above and adhered to the base layer. In some embodiments, the adherent device further comprises a thin, flexible, stretchable underlayer disposed below and adhered to the base layer, and the underlayer is configured to adhere to the skin of the subject. In some embodiments the adherent device further comprises a stiffening structure disposed over and coupled to a perimeter of the base layer and configured to stiffen the perimeter edge of the base layer. The adherent device may comprise a compliant connection between the circuit carrier and the base layer.

According to some embodiments, an adherent device to monitor a subject having a skin comprises a stretchable base layer having an upper side and a lower side and an adhesive coating on the lower side to adhere the base layer to the skin of a subject. The base layer has at least two openings extending therethrough, each of the at least two openings having a size. A stretchable covering layer is positioned above and adhered to the base layer with an adhesive to define at least two pockets. The adherent device further comprises a flexible circuit support that includes a first portion and a second portion, the first portion of the support adhered between the stretchable base layer and the stretchable covering layer, the second portion extending from the first portion. At least two electrodes are disposed on the first portion of the flex circuit support. The adherent device further includes at least two gels, and each gel and each electrode are positioned within a corresponding pocket, each gel having a size larger than the size of the respective opening to retain said gel substantially within said pocket between the base layer and the covering layer. The adherent device further includes a circuit carrier supported with the stretchable base layer, the circuit carrier holding electronic components electrically connected to the at least two electrodes with the second portion of the flexible circuit support to relieve strain when the stretchable base layer stretches with the skin of the subject, the electronic components configured to measure at least one physiologic signal of the subject.

According to some embodiments, a method of manufacturing an adherent device to adhere to a skin of a subject comprises providing a stretchable base layer having an upper side and a lower side and an adhesive coating on the lower side to adhere the base layer to the skin of a subject. The base layer has at least two openings extending therethrough, each of the at least two openings having a size. The method further comprises providing a flexible circuit support having at least two electrodes and traces of electrically conductive material disposed thereon, providing at least two gels, and providing a stretchable covering layer. The method further comprises positioning the flexible circuit support and at least two gels between the stretchable base layer and the stretchable covering layer, and adhering the stretchable base layer to the stretchable covering layer to form at least two pockets, wherein each pocket has one of the at least two gels and one of the electrodes disposed therein. The method also includes coupling a circuit carrier to the at least two electrodes with the flexible circuit support.

According to some embodiments, a method of monitoring a patient having a skin comprises adhering a stretchable base layer affixed to a stretchable covering layer to the skin of the patient. The stretchable base layer and the stretchable covering layer define a plurality of pockets with gels and electrodes disposed therein and the electrodes are coupled to the skin with the gels disposed in the pockets. The method further comprises measuring signals from the electrodes to monitor the patient.

According to some embodiments, an adherent device to adhere to a skin of a subject comprises means for adhering to a skin of a subject, and a circuit carrier means coupled to the means for adhering to measure at least one physiologic signal of the subject.

Other embodiments are also described and claimed.

DETAILED DESCRIPTION OF THE INVENTION

Embodiments of the present invention relate to subject monitoring and/or therapy. Although embodiments make specific reference to monitoring impedance and electrocardiogram signals with an adherent device, the system methods and device described herein may be applicable to any application in which physiological monitoring and/or therapy is used for extended periods, for example wireless physiological monitoring for extended periods.

Embodiments of the present invention can be particularly well suited for use with an adherent device that comprises a support, for example a patch that may comprise stretchable tape, such that the support can be configured to adhere to the subject and support the electronics and sensors on the subject. The support may also be porous and breathable so as to allow water vapor transmission, for example as described U.S. Pat. Pub. No. 2009/0076363, the full disclosure of which is incorporated herein by reference and suitable for combination in accordance with some embodiments of the present invention described herein. The adherent device may comprise a cover and electronic components disposed on a carrier coupled to the support so as to provide strain relief, such that the support can stretch and flex with the skin of the subject. The embodiments described herein can be particularly useful to inhibit motion of the electronics circuitry carrier when the support stretches and flexes, so as to decrease localized loading of the support that may contribute to peeling. When forces are localized near an edge of the adherent device, for example when the carrier moves against a cover, the localized forces may cause peeling near the edge, and the embodiments described herein can inhibit such localized forces with a compliant structure that inhibits motion of the carrier relative to the support and also allows the support to stretch.

Figure 1:
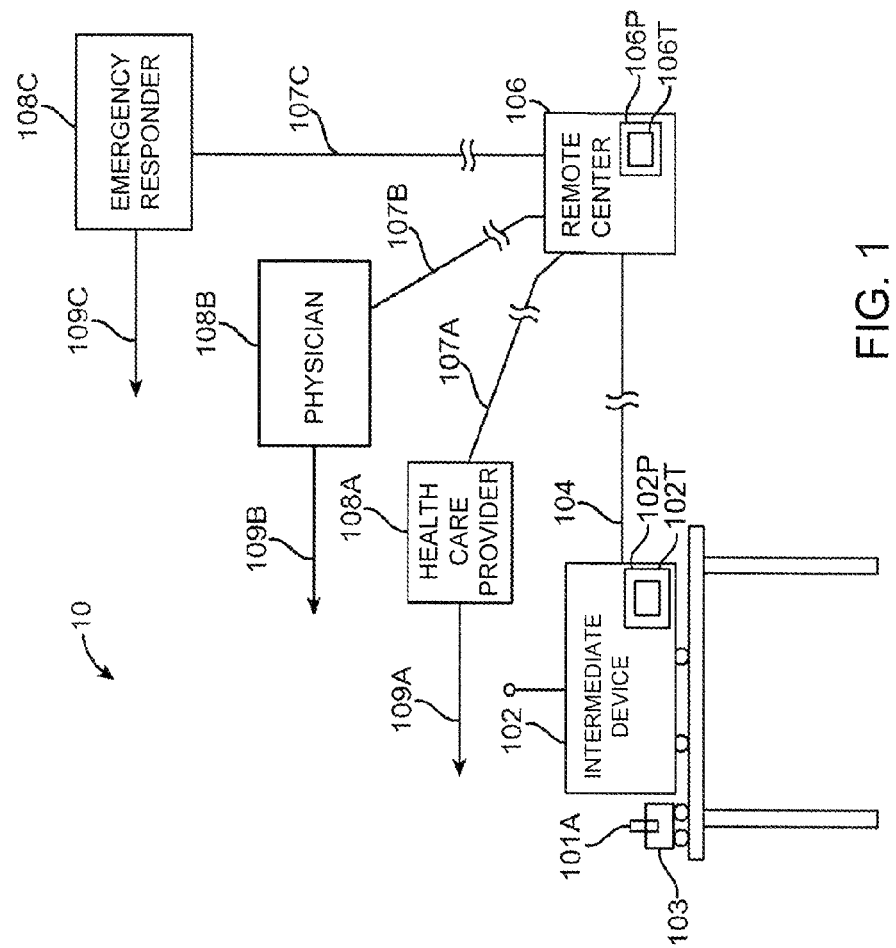
FIG. 1 shows a patient and a monitoring system comprising an adherent device, in accordance with embodiments of the present invention.
Figure 1:
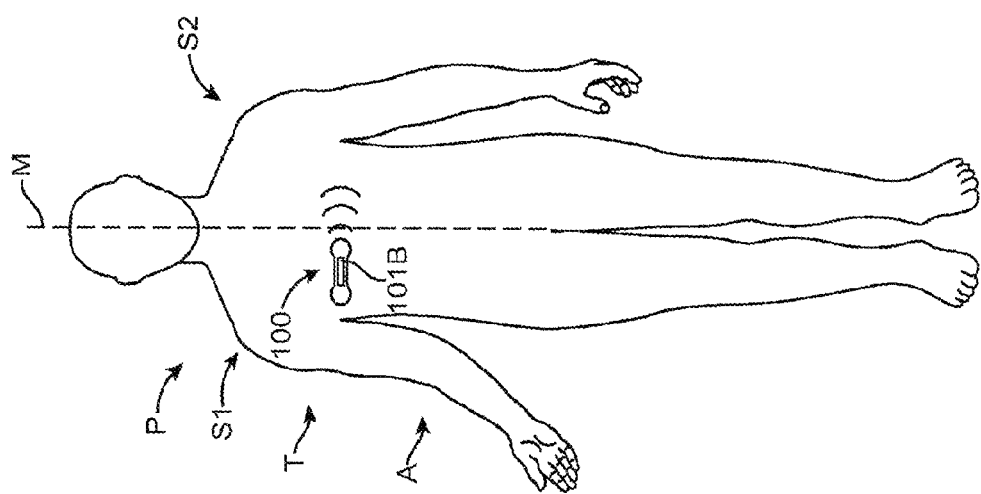

FIG. 1 shows an example subject, patient P, and a monitoring system 10. Patient P comprises a midline M, a first side S1, for example a right side, and a second side S2, for example a left side. Monitoring system 10 comprises an adherent device 100. Adherent device 100 can be adhered to a patient P at many locations, for example thorax T or arm A of patient P. In many embodiments, the adherent device may adhere to one side of the patient, from which side data can be collected. Work in relation with embodiments of the present invention suggests that location on a side of the patient can provide comfort for the patient while the device is adhered to the patient.

Monitoring system 10 includes components to transmit data to a remote center 106. Remote center 106 can be located in a different building from a subject such as patient P, for example in the same town as the subject, and can be located as far from the subject as a separate continent from the subject, for example the subject located on a first continent and the remote center located on a second continent. Adherent device 100 can communicate wirelessly to an intermediate device 102, for example with a single wireless hop from the adherent device on the subject to the intermediate device. Intermediate device 102 can communicate with remote center 106 in many ways, for example with an internet connection and/or with a cellular connection. In many embodiments, monitoring system 10 comprises a distributed processing system with at least one processor comprising a tangible medium on device 100, at least one processor on intermediate device 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the subject's thorax and contains sensing electrodes, battery, memory, logic, and wireless communication capabilities. In some embodiments, the device can communicate with the remote center, via the intermediate device in the subject's home. In some embodiments, the remote center 106 receives the patient data and applies a patient evaluation and/or prediction algorithm. When a flag is raised, the center may communicate with the patient, hospital, nurse, and/or physician to allow for therapeutic intervention, for example to prevent decompensation.

In many embodiments, the adherent device may comprise a reusable electronics module with replaceable patches, and each of the replaceable patches may include a battery. The module may collect cumulative data for approximately 90 days and/or the entire adherent component (electronics+patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the subject.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, heart rate variability (hereinafter "HRV"), heart rate turbulence (hereinafter "HRT"), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture. Additional details about the use of an adherent patch to measure particular physiologic signals may be found in co-pending U.S. patent application Ser. No. 12/209,273 (publication 2009/0076363) and Ser. No. 12/209,288 (publication 2009/0076345), both filed on Sep. 12, 2008 and titled "Adherent Device with Multiple Physiologic Sensors"

The adherent device can wirelessly communicate with remote center 106. The communication may occur directly (via a cellular or Wi-Fi network), or indirectly through intermediate device 102. Intermediate device 102 may consist of multiple devices, which can communicate wired 104 or wirelessly to relay data to remote center 106.

In many embodiments, instructions are transmitted from remote site 106 to a processor supported with the adherent patch on the subject, and the processor supported with the subject can receive updated instructions for the subject treatment and/or monitoring, for example while worn by the subject.

In order for complete and reliable data to be gathered by system 10, and for optimal subject comfort, it is desirable that adherent device 100 remain securely attached to subject for a predetermined period of time, for example one week, or two weeks or more. If adherent device 100 becomes dislodged prematurely, such that one or more of the sensing electrodes no longer makes secure contact with the subject's skin, valuable medical or other data may be lost. For example, a dislodged adherent device 100 may also need to be replaced, causing discomfort for a patient, inconvenience for medical personnel, and unwanted expense.

Various adhesion failure mechanisms have been noted. Normal subject activity may result in adherent device 100 being stretched, bumped, jostled, or otherwise moved in a way that tends to stress the adhesive joint with the subject's skin. This may be especially true for an adherent device that is worn for a long period of time, during which the subject may wish to carry on normal activities, including exercise, bathing, and the like. The edges of the support patch may be especially prone to separation from the skin, and may form pathways for ingress of moisture, which can accelerate the deterioration of the adhesive bond between the adherent device and the skin. The difficulty of maintaining a secure bond to the subject's skin may be further exacerbated as it becomes desirable to add new features and capabilities to a device such as adherent device 100. For example, in order to extend the working life of adherent device 100 or to provide sophisticated features, it may be desirable to include a battery having considerable weight, and additional electronics or packaging as compared with previous designs. The combined weight of the battery and electronics may be as much as 60 grams or more, such that jostling of the unit may impart significant inertial loads on the bond with the subject's skin. In addition, the position of the adherent device may affect the durability of the adhesive bond with the subject's skin. For example, especially useful electrocardiogram readings may be obtained by a device placed between a patient's left clavicle and left nipple. However, this area is also prone to stretching, and may present a difficult site for long-term adhesion. Even if an alternative site is used, for example along the patient's rib line, enhanced adhesion durability is desirable.

In addition to the medical setting described above, embodiments of the present invention may also be used in non-medical settings, and on subjects other than human medical patients. For example, an adherent device according to embodiments of the invention may be used to monitor the heart rate or other data of an athlete during exercise. In another setting, an adherent device according to embodiments of the invention may be used to monitor an animal for agricultural research, veterinary medical testing or treatment, or other purposes. For the purposes of this disclosure, a subject is any human or animal to which an adherent device according to embodiments of the invention may be adhered, for any purpose. While certain example uses of adherent devices are described herein in relation to monitoring or treatment of a medical patient, the appended claims are not so limited. Whatever the setting or subject, embodiments of the present invention provide improved durability of the adhesive bond between the adherent device and the subject's skin, as compared with prior adherent devices.

Figure 2A:
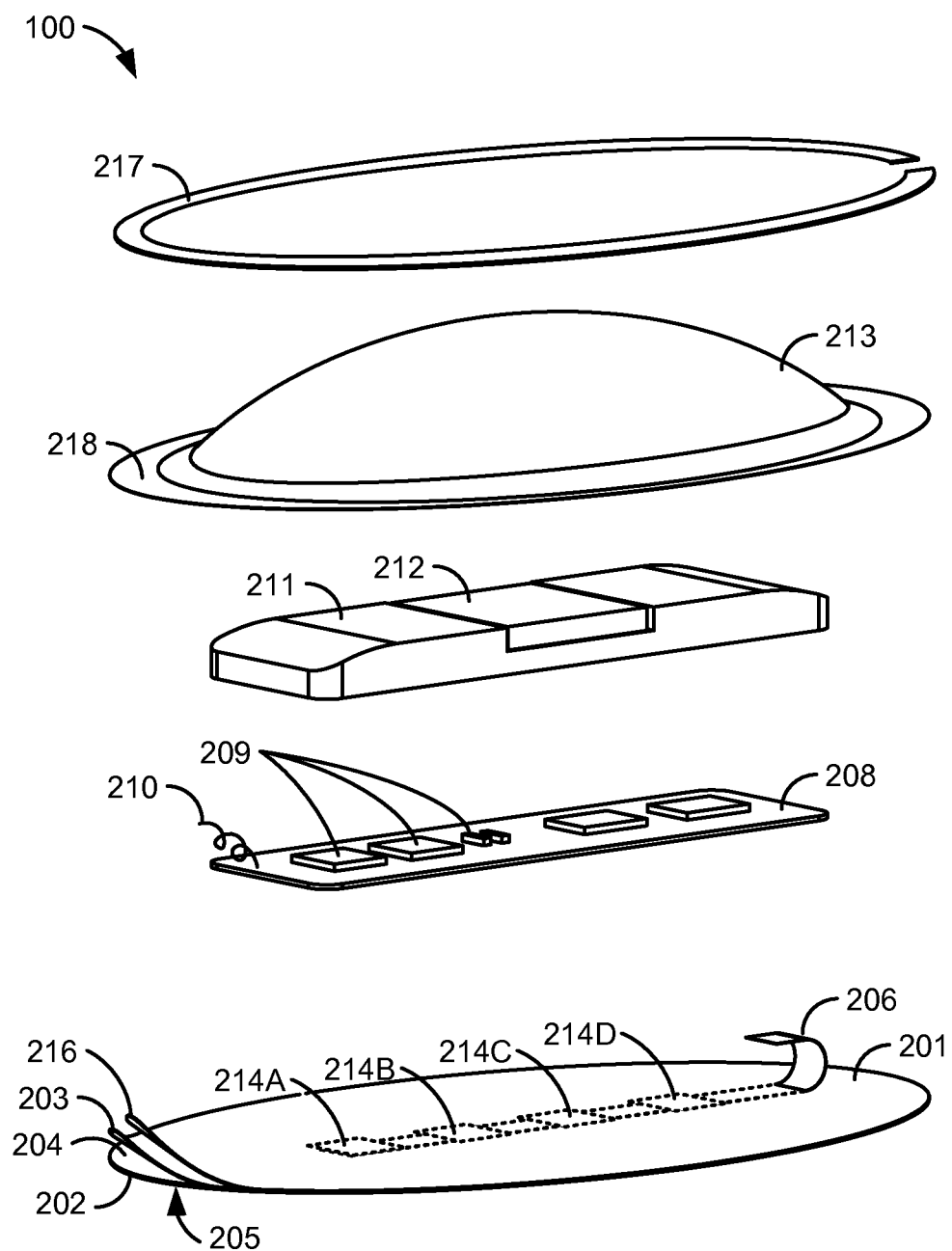
FIG. 2A shows a partial exploded perspective view of an adherent device as in FIG. 1, in accordance with embodiments of the invention.
Figure 2B:
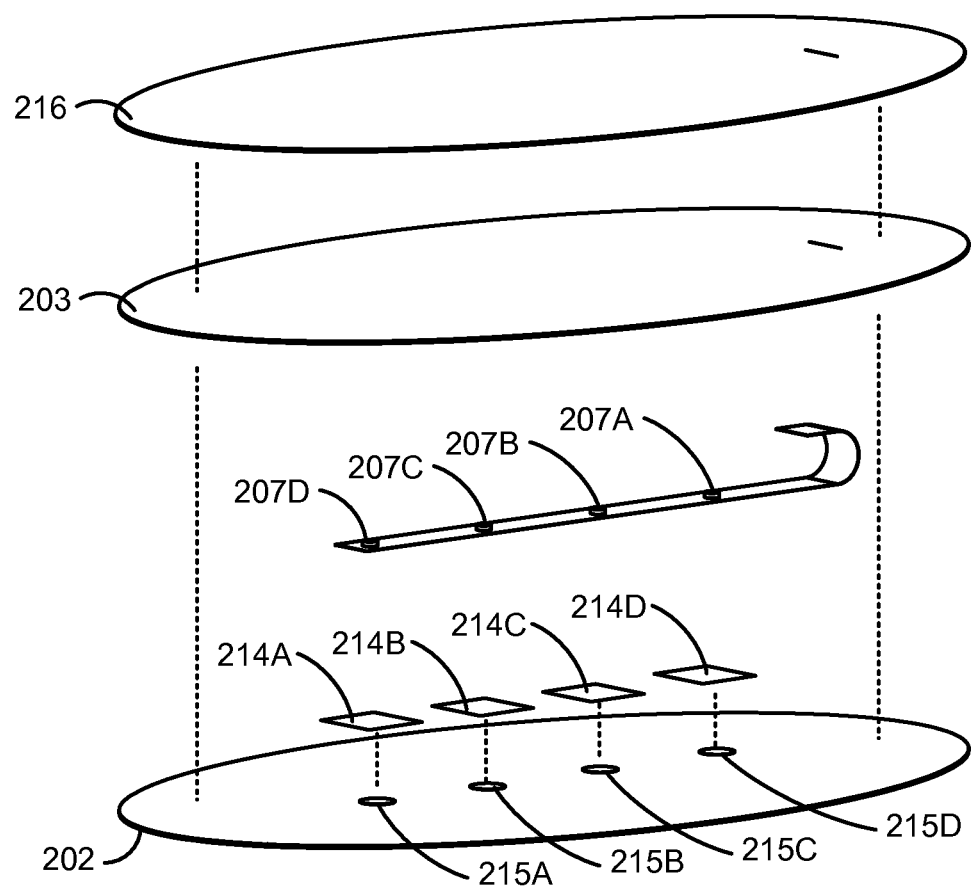
FIG. 2B illustrates an exploded view of a support patch, according to embodiments of the invention.

FIG. 2A shows a partial exploded perspective view of adherent device 100 as in FIG. 1, in accordance with embodiments of the invention. Adherent device 100 comprises a support patch 201, which may further comprise a base layer 202 and a covering layer 203. Base layer 202 is stretchable, and has an upper side 204 and a lower side 205, and an adhesive coating on lower side 205 to adhere base layer 202 to the skin of a subject. Covering layer 203 is also stretchable, and is positioned above and adhered to base layer 202. FIG. 2B illustrates an exploded view of support patch 201, according to embodiments of the invention. As is best seen in FIG. 2B, a flexible circuit 206 includes at least two electrodes, for example electrodes 207A, 207B, 207C, and 207D that during use are in electrical contact with the skin of the subject. Flexible circuit 206 may also sometimes be called a flexible circuit support. Flexible circuit 206 electrically connects electrodes 207A, 207B, 207C, and 207D to a circuit carrier 208, which holds electronic components 209 configured to measure at least one physiologic signal of the subject. Electronic components 209 may include an antenna 210 so that adherent device 100 can communicate its readings for remote monitoring. Circuit carrier 208 may be mechanically connected to and supported by base layer 202 by any suitable means, including those discussed in more detail below.

Adherent device 100 may further comprise a housing 211 that fits over electronic components 209, providing protection, insulation, and cushioning for electronic components 209. Housing 211 may further include features for holding a battery 212. Housing 211 may be made, for example of a soft silicone rubber. In other embodiments, housing 211 may comprise an encapsulant over electronic components 209 and circuit carrier 208. Housing 211 may provide protection of electronic components 209 from moisture.

Adherent device 100 may also comprise a cover 213 adhered to support patch 201. Cover 213 may comprise any known biocompatible cover, casing and/or housing materials, such as elastomers, for example silicone. The elastomer may be fenestrated to improve breathability. In some embodiments, cover 213 may comprise other breathable materials, for example a cloth including polyester, polyamide, nylon and/or elastane (Spandex™). The breathable fabric may be coated or otherwise configured to make it water resistant, waterproof, for example to aid in wicking moisture away from the patch, or to inhibit liquids from reaching electronic components 209.

While adherent device 100 is shown as generally oblong and having a length of about two to three times its width, this is not a requirement. One of skill in the art will recognize that other shapes are possible for an adherent device according to embodiments of the invention. For example, support patch 201 could be round, elliptical or oblong with a length only slightly larger than its width, square, rectangular, or some other shape. And while electrodes 207A, 207B, 207C, and 207D are illustrated as being arranged linearly, this is also not a requirement. One of skill in the art will recognize that electrodes 207A, 207B, 207C, and 207D could be arranged in any pattern suitable for the intended use of adherent device 100, including in a circular, oblong, square, rectangular, or other pattern.

Referring again to FIG. 2B, base layer 202 includes at least two openings, in this case four openings 215A, 215B, 215C, and 215D, each corresponding to one of electrodes 207A, 207B, 207C, and 207D. Each opening is of a certain size. Gels 214A, 214B, 214C, and 214D are placed at the openings, between base layer 202 and covering layer 203. Each of gels 214A, 214B, 214C, and 214D comprises a hydrogel patch of electrically conductive gel material that enhances electrical conductivity between its respective electrode and the skin of the subject. For example, the gels 214A, 214B, 214C, and 214D may be made of hydrogel adhesive 9880 available from the 3M Company of St. Paul, Minn., USA, or another suitable material.

Each of gels 214A, 214B, 214C, and 214D is larger than its respective opening 215A, 215B, 215C, or 215D, such that when covering layer 203 and base layer 202 are adhered together, a pocket is formed over each of openings 215A, 215B, 215C, and 215D, with one of gels 214A, 214B, 214C, and 214D retained in each respective pocket.

Preferably, base layer 202, covering layer 203, or both are thin, flexible, and stretchable to stretch with the skin of the subject and conform to folds of the skin of the subject. For example, either or both of these layers may be made of MED 5021 polyurethane film available from Avery Dennison Corporation of Pasadena, Calif., USA, or Tegaderm™ film available from the 3M Company of St. Paul, Minn., USA. Other suitable materials may be used.

In some embodiments, support patch 201 may further include an overlayer 216 disposed above and adhered to covering layer 203. Overlayer 216 is also preferably thin, flexible, and stretchable. For example, overlayer 216 may be made of a woven fabric.

Referring again to FIG. 2A, gels 214A, 214B, 214C, and 214D are preferably placed under covering layer 203 (and overlayer 216, if present). Flexible circuit 206 may also be positioned under covering layer 203, as indicated by the broken line depiction of part of flexible circuit 206 in FIG. 2B. Gels 214A, 214B, 214C, and 214D may thus be retained in pockets between base layer 202 and covering layer 203.

Adherent device 100 may further comprise a stiffening structure such as stiffening structure 217 shown in FIG. 2A. In this example embodiment, stiffening structure 217 is configured to adhere to the top of cover 213, at an outer area 218 of cover 213. As assembled, stiffening structure 217 is then coupled to a common perimeter of the base and covering layers, so that the perimeter edges of the base and covering layers are stiffened, for example to prevent curling or unintentional adhesion of the lower side 205 of base layer 202 to itself. Stiffening structure 217 may be made of a material that is stiffer than the materials used in base patch 201, but still compliant enough to allow base patch 201 to conform to the subject's skin as the patch is adhered to the skin. For example, stiffening structure 217 may be made from a vinyl sheet. Stiffening structure 217 may also be configured to be removable after adherent device 100 is adhered to the subject's skin. For example, stiffening structure 217 may include an adhesive configured to hold stiffening structure 217 in place during application of adherent device 100 to the subject, but to release easily without dislodging adherent device 100 from the subject's skin. In this way, stiffening structure 217 may aid in achieving a secure adhesion of adherent device 100 to the subject, but not interfere with the ability of support patch 201 to conform to wrinkles, folds, and other movements of the subject's skin while adherent device 100 is worn.

Figure 2C:
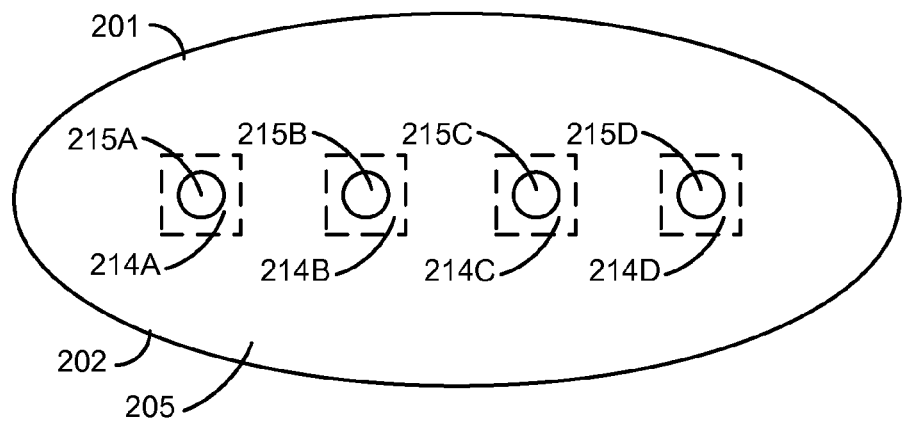
FIG. 2C shows a bottom view of the support patch of FIG. 2B.

FIG. 2C shows a bottom view of support patch 201, with bottom lower side 205 of base layer 202 visible. Also visible are openings 215A, 215B, 215C, and 215D, exposing portions of gels 214A, 214B, 214C, and 214D. Other portions of gels 214A, 214B, 214C, and 214D are behind base layer 202, in pockets formed between base layer 202 and covering layer 203.

Figure 3:
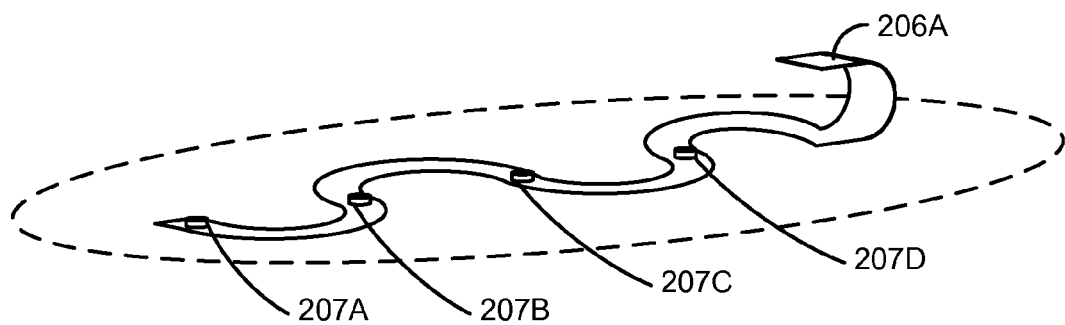
FIG. 3 shows a flexible circuit that is configured to be stretchable, in accordance with embodiments of the invention.

In some embodiments, flexible circuit 206 may be made of a flexible material such as polyimide, polyester, or another base material, having circuit traces formed in or on the base material. The circuit traces may be, for example, made of copper, a copper alloy, silver ink, or another conductive material. In one preferred embodiment, flexible circuit 206 comprises a polyester base and traces formed of silver conductive ink. In some embodiments, flexible circuit 206 may be configured to be stretchable, as well as flexible. Even if the material of the flexible circuit 206 is not inherently stretchable, the flexible circuit may be made effectively stretchable by properly configuring its geometric shape. For example, at least the portion of flexible circuit 206 in contact with support patch 201 may have a serpentine shape that allows support patch 201 to stretch and conform itself to the skin of the subject to which adherent device 100 is adhered, without being unduly constrained by flexible circuit 206. A flexible circuit 206A having this characteristic is shown in FIG. 3. Other configurations may be used as well. For example, flexible circuit 206A may have a sawtooth shape, or another shape that enables stretching of the flexible circuit 206A.

Figure 4:
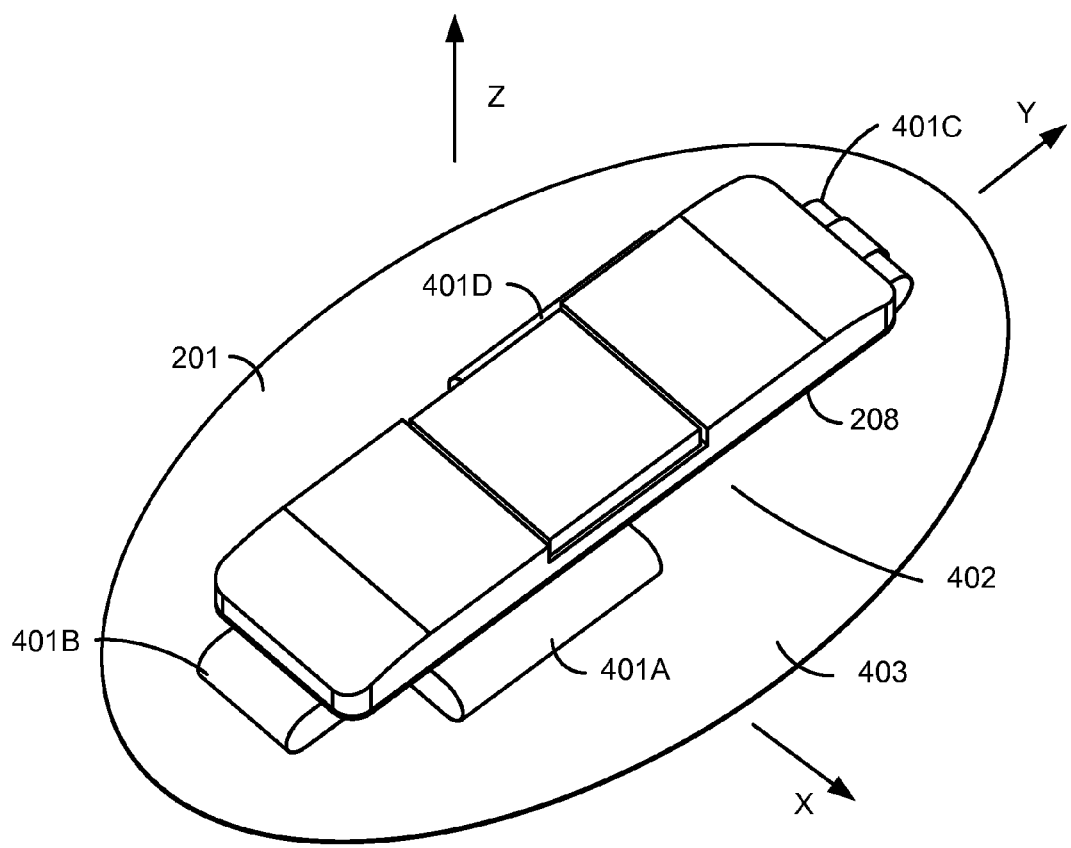
FIG. 4 illustrates a compliant connection between a circuit carrier and a base layer, in accordance with embodiments of the invention.

As was mentioned previously, circuit carrier 208 may have a compliant connection to base layer 202. One exemplary kind of compliant connection is illustrated in FIG. 4. In this connection, bridging loops 401A, 401B, 401C, and 401D connect from support patch 201 (which includes base layer 202) to circuit carrier 208. Loops 401A, 401B, 401C, and 401D may be made, for example, of a plastic reinforced paper, a plastic film, a fabric, metal, or any other suitable material. Preferably, loops 401A, 401B, 401C, and 401D permit relatively free rotation of circuit carrier 208 about the X and Y axes illustrated in FIG. 4, but constrain the rotation of circuit carrier 208 about the Z axis. Because each of loops 401A, 401B, 401C, and 401D connects to support patch 201 at an inner portion 402 rather than at an outer portion 403 of support patch 201, loads imparted to support patch 201 tend not to disturb the vulnerable perimeter of support patch 201, where detachment from the subject's skin is especially likely to start. More detail about compliant connections between circuit carrier 208 and base layer 202 may be found in copending provisional U.S. patent application 61/241,713, filed Sep. 11, 2009 and titled "Electronics Integration in Adherent Patch for Physiologic Monitoring", the entire disclosure of which is hereby incorporated by reference for all purposes.

In some embodiments, base layer 202, covering layer 203, or their combination may be breathable. For example, the combination of base layer 202 and covering layer 203 may have a moisture vapor transmission rate of at least 100 g/m$^2$/day.

Figure 5:
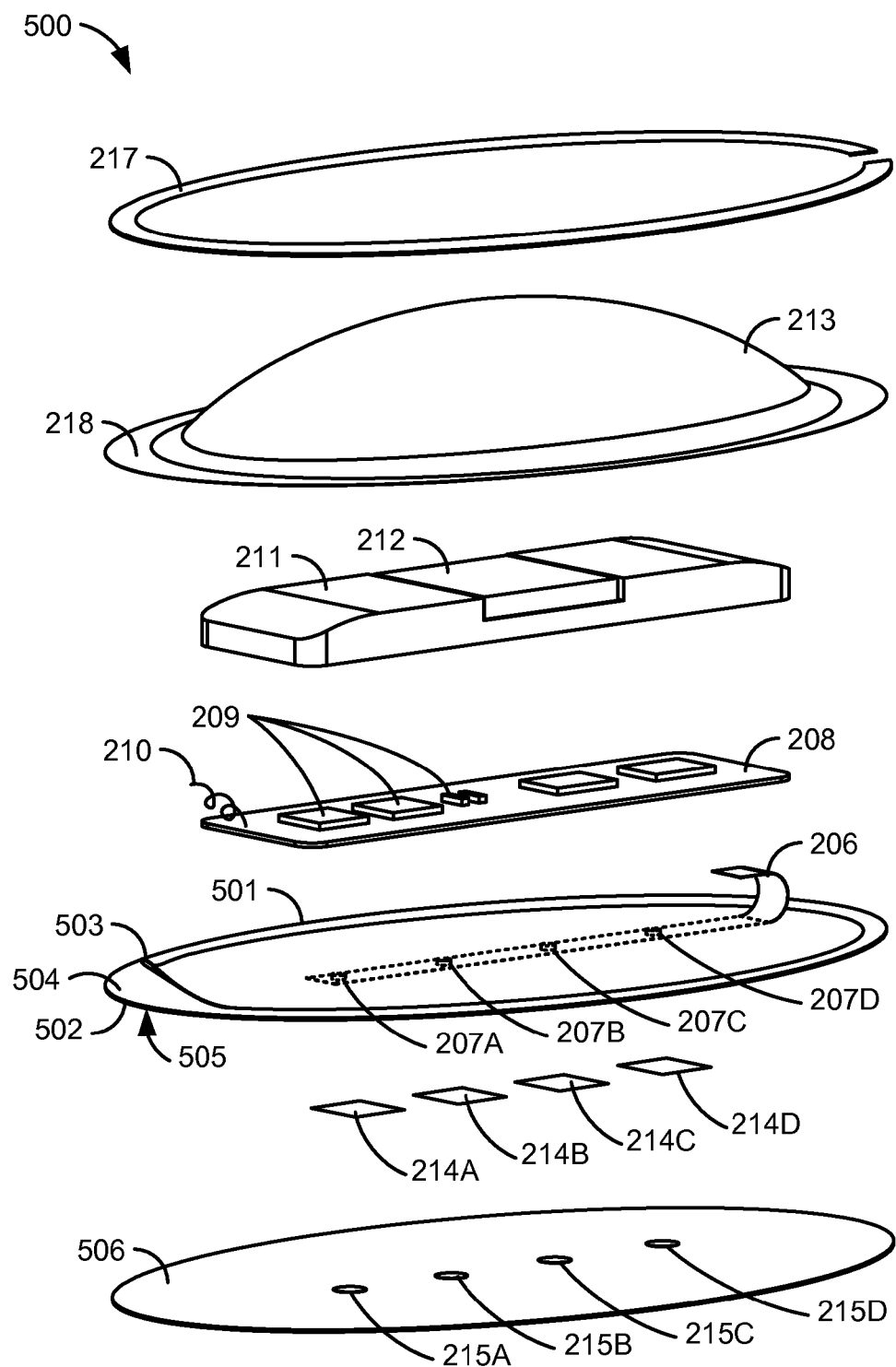
FIG. 5 illustrates an exploded view of an adherent device in accordance with additional embodiments of the invention.

FIG. 5 illustrates an exploded view of an adherent device 500 in accordance with additional embodiments of the invention. Adherent device 500 includes several components similar to those in adherent device 100, and similar components are given the same reference numbers in FIG. 5. Adherent device 500 may include different combinations of layers than adherent device 100.

Adherent device 500 comprises a support patch 501 that includes a base layer 502. Base layer 502 has an upper side 504 and a lower side 505. Lower side 505 includes an adhesive coating. At least one electrode, in this example four electrodes 207A, 207B, 207C, and 207D are affixed to base layer 502 and connected to flexible circuit 206. Besides being flexible, flexible circuit 206 may also be configured to be stretchable, for example due to its geometric configuration. In some embodiments, a portion of flexible circuit 206 may have a serpentine or sawtooth shape. Circuit carrier 208 holds electronic components 209, which may include an antenna 210. Electronic components 209 are electrically connected to electrodes 207A, 207B, 207C, and 207D and are configured to measure at least one physiologic signal of a subject to which adherent device 500 is adhered.

A stiffening structure 217 may be disposed over and coupled, directly or indirectly, to a perimeter area of base layer 502, to stiffen the perimeter edge of base layer 502. In some embodiments, a cover 213 is disposed over circuit carrier 208 and coupled at a perimeter 218 to base layer 502. In that case, stiffening structure 217 is disposed over and coupled to cover 213, and is therefore indirectly coupled to base layer 502. Cover 213 is preferably soft and flexible, and may be made of a material configured to inhibit liquids from reaching electronic components 209.

Similarly, in some embodiments, an overlayer 503 may be disposed above and adhered to base layer 502. Overlayer 503 is preferably thin, flexible, and stretchable, and may be made of a woven cloth or another suitable material. When overlayer 503 is present, stiffening structure 217 is also disposed over and coupled to the perimeter of overlayer 503, and stiffens at least the perimeter edges of the base layer and overlayer. All of the layers of a support patch such as support patch 501 or support patch 201 may be coextensive, having their edges aligned as was shown in FIG. 2C. Alternatively, one or more layers in a support patch may not be coextensive with the others. For example, overlayer 503 is slightly smaller than base layer 502, so that the edges of base layer 502 extend beyond the edges of overlayer 503. This arrangement may further reduce the stresses on the edge of base layer 502, thus promoting long adhesion to the subject to which adherent device 500 is adhered. This arrangement may be used in any of the embodiments described herein.

Adherent device 500 may comprise one or more gel patches 214A, 214B, 214C, and 214D, one gel disposed under each of electrodes 207A, 207B, 207C, and 207D. Gel patches 214A, 214B, 214C, and 214D enhance electrical conductivity between electrodes 207A, 207B, 207C, and 207D and the skin of a subject to which adherent device 500 is adhered.

In some embodiments, lower side 505 of base layer 502 is configured to adhere to the skin of a subject. In that configuration, gel patches 214A, 214B, 214C, and 214D are captured between base layer 502 and the subject's skin. Optionally, an underlayer 506 may be provided, adhered to lower side 505 of base layer 504, and configured to adhere to the skin of a subject. Preferably, underlayer 506 is also thin, flexible, and stretchable. For example, base layer 202, underlayer 506, or both may be made of MED 5021 polyurethane film available from Avery Dennison Corporation of Pasadena, Calif., USA, or Tegaderm™ film available from the 3M Company of St. Paul, Minn., USA. Other suitable materials may be used. Underlayer 506 may comprise openings 215A, 215B, 215C, and 215D, and may capture gels 214A, 214B, 214C, and 214D in pockets formed between base layer 502 and underlayer 506.

As in adherent device 100, adherent device 500 may include a compliant connection between circuit carrier 208 and base layer 502, for example a compliant connection as shown in FIG. 4 and described previously.

Figure 6:
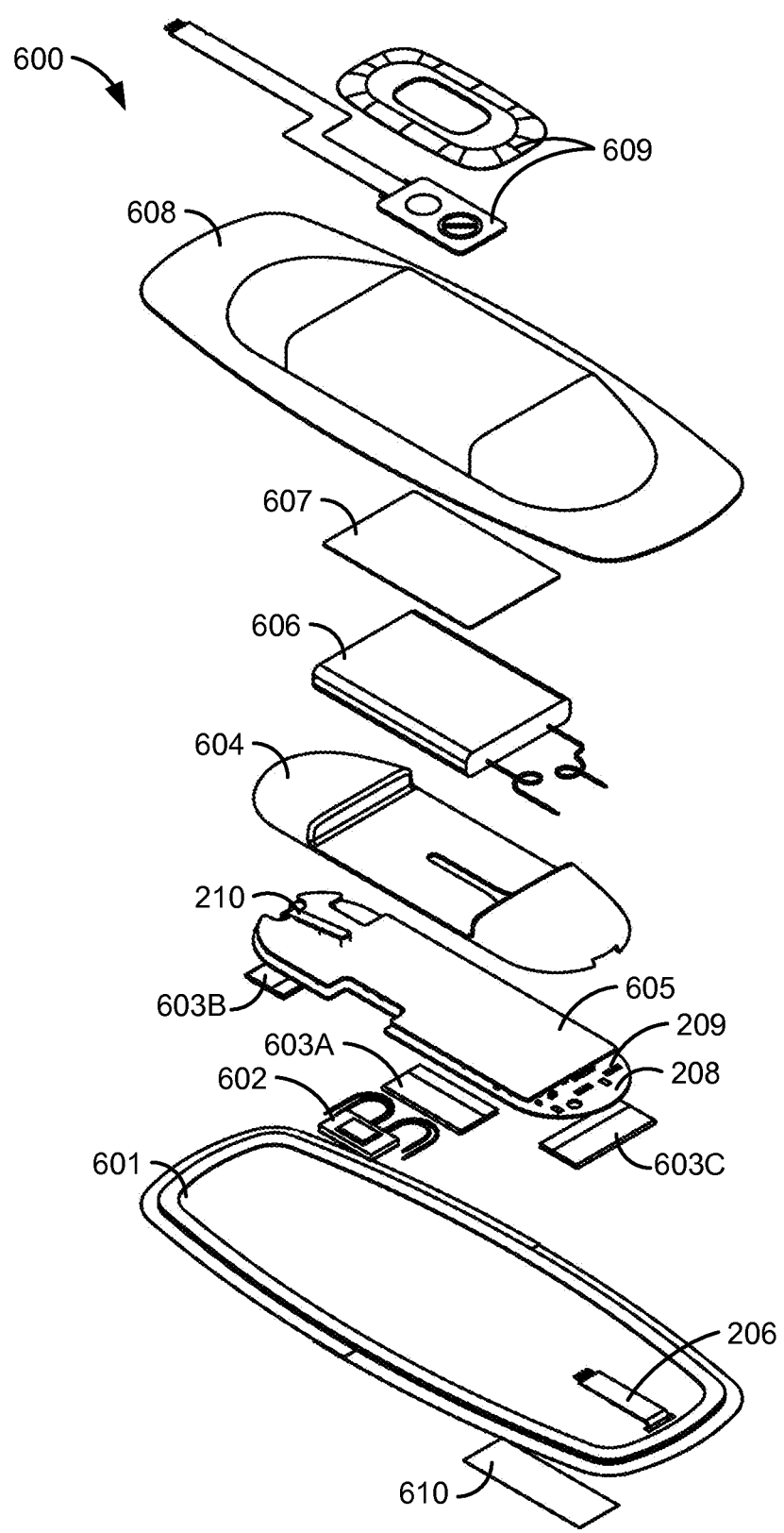
FIG. 6 illustrates an exploded oblique view of an adherent device in accordance with additional embodiments of the invention.

FIG. 6 illustrates an exploded oblique view of an adherent device 600 in accordance with additional embodiments of the present invention. In this embodiment, a support patch 601 may be configured to adhere to a subject's skin, and may be a support patch as in any of the embodiments described above. Support patch 601 may include a base layer, a covering layer, an overlayer, an underlayer, or any workable combination of these. Support patch 601 may include one or more electrodes (not visible in FIG. 6) electrically connected to a flexible circuit 206. A label 610 may be affixed to support patch 601. A circuit carrier 208 holds various electronic components 209, which may include a processor, memory, wireless communication circuitry, an antenna 210, and other electronic components. Adherent device 600 may also include a temperature or heat flux sensor 602. Bridging loops 603A, 603B, 603C (and a fourth bridging loop not visible in FIG. 3B) are affixed to support patch 201 and to circuit carrier 208, and form a compliant structure that compliantly restrains motion of circuit carrier 208 with respect to support patch 601 in some degrees of freedom more stiffly than in other degrees of freedom. A housing 604 and protector 605 may insulate, cushion, or otherwise protect circuit carrier 208. The adherent device may further comprise a battery 606 or other energy source, a battery cover 607, a cover 608, and a display 609.

While exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. An adherent device to adhere to a skin of a subject, comprising: a stretchable base layer having an upper side and a lower side and an adhesive coating on the lower side to adhere the base layer to the skin of the subject, the base layer having at least two openings extending therethrough, each of the at least two openings having a size; a stretchable covering layer positioned above and adhered to the base layer with an adhesive to define at least two pockets, wherein the stretchable covering layer is thin, flexible, and configured to stretch with the skin of the subject; at least two gels, wherein each gel is positioned within one of the corresponding pockets, each gel having a size larger than the size of the at least two openings to retain said gel substantially within said corresponding pocket; a flexible circuit that includes at least two electrodes in contact with the at least two gels, the flexible circuit including a first portion located on the upper side of the stretchable base layer and a second portion that extends away from the first portion and through an opening in the stretchable covering layer; a circuit carrier positioned above the stretchable covering layer and supported with the stretchable base layer to measure at least one physiologic signal of the subject, wherein the circuit carrier is connected to the at least two electrodes via the second portion extending through an opening in the stretchable covering layer; and a compliant connection that includes a plurality of bridging loops formed between the upper side of the stretchable base layer and the circuit carrier that permits at least some movement of the circuit carrier in a plane parallel to the stretchable base layer.

2. An adherent device to monitor a subject having a skin, comprising: a stretchable base layer having an upper side and a lower side and an adhesive coating disposed on the lower side to adhere the base layer to the skin of the subject, the base layer having at least two openings extending therethrough, each opening having a size; a flexible circuit having at least two electrodes disposed thereon, each electrode positioned with a respective one of the at least two openings to couple to the skin of the subject the flexible circuit including a first portion located adjacent to the upper side of the stretchable base layer and a second portion that extends away from the stretchable base layer through an opening in a stretchable covering layer; at least two gels positioned with the at least two openings in the base layer, each gel having a size larger than the size of said each opening; the stretchable covering layer positioned above the at least two gels and adhered to the base layer, such that each gel is constrained substantially within a corresponding pocket disposed between the base layer and the covering layer, wherein the stretchable covering layer is thin, flexible, and configured to stretch with the skin of the subject; a circuit carrier positioned above the stretchable covering layer and holding electronic components electrically connected to the at least one electrode via the second portion of with the flexible circuit to measure at least one physiologic signal of the subject; and a compliant connection that includes a plurality of bridging loops formed between an upper side the stretchable base layer and the circuit carrier that permits at least some movement of the circuit carrier in a plane parallel to the stretchable base layer.

3. The adherent device of claim 2 wherein each of the gels and each of the pockets is sized larger than a corresponding opening of the stretchable base layer to retain said gel in said pocket when the stretchable base layer is adhered to the skin of the subject.

4. The adherent device of claim 2 wherein the stretchable base layer comprises a thin, flexible, stretchable base layer to stretch with the skin of the subject and conform to folds of the skin of the subject, and wherein the stretchable covering layer is configured to conform to folds of the skin of the subject.

5. The adherent device of claim 2, further comprising a thin, flexible, stretchable overlayer disposed above and adhered to the covering layer.

6. The adherent device of claim 2, wherein the first portion of the flexible circuit is formed of a substantially non-stretchable material, and has a serpentine, sawtooth, or other shape that geometrically configures the flexible circuit to be stretchable along a length of the adherent device.

7. The adherent device of claim 2, wherein the first portion of the flexible circuit is disposed between the base layer and the covering layer.

8. An adherent device, comprising:
- a thin, flexible, stretchable base layer having an upper side and a lower side and an adhesive coating on the lower side to adhere to the skin of a subject;
- at least one electrode affixed to the base layer and capable of electrically coupling to the skin of the subject;
- a flexible circuit connected to the at least one electrode, wherein the flexible circuit includes a first portion located adjacent to the upper side of the stretchable base layer and a second portion that extends away from the first portion, wherein the second portion of the flexible circuit includes a loop shape to relieve strain when the stretchable base layer stretches with the skin of the subject;
- a circuit carrier holding electronic components electrically connected to the at least one electrode via the second portion of the flexible circuit and configured to measure at least one physiologic signal of the subject;
- a compliant connection that includes a plurality of loops formed between the upper side of the stretchable base layer and the circuit carrier that permits at least some movement of the circuit carrier in a plane parallel to the stretchable base layer, wherein the second portion of the flexible circuit extends around an outer circumference of one of the plurality of loops; and
- a stiffening structure disposed above and coupled to a perimeter of the base layer and configured to stiffen the perimeter edge of the base layer, wherein the stiffening structure is removable.

9. The adherent device of claim 8, further comprising a thin, flexible, stretchable overlayer disposed above and adhered to the base layer, the stiffening structure disposed over and coupled to a common perimeter of the base layer and overlayer and configured to stiffen the perimeter edge of the base layer and overlayer.

10. The adherent device of claim 8, further comprising a gel patch under each electrode, wherein each gel patch enhances electrical conductivity between its respective electrode and the skin of the subject.

11. The adherent device of claim 8, wherein the flexible circuit is configured to be stretchable.

12. An adherent device, comprising:
- a thin, flexible, stretchable base layer having an upper side and a lower side and an adhesive coating on the lower side configured to adhere to a skin of a subject;
- at least one electrode affixed to the base layer and capable of electrically coupling to the skin of a subject;
- a flexible circuit having a first portion located on the upper side of the stretchable base layer that is connected to the at least one electrode and a second portion that extends away from the stretchable base layer, wherein the first portion of the flexible circuit is formed of a substantially non-stretchable material, and has a serpentine, sawtooth, or other shape that geometrically configures the flexible circuit to be stretchable along a length of the adherent device, and wherein the second portion includes a loop shape to relieve strain when the stretchable base layer stretches with the skin of the subject;
- a circuit carrier positioned above and coupled to the flexible circuit, the circuit carrier holding electronic components electrically connected to the at least one electrode via the second portion of the flexible circuit flexible circuit and configured to measure at least one physiologic signal of the subject; and
- a compliant connection formed between the stretchable base layer and the circuit carrier that permits at least some movement of the circuit carrier in a plane parallel to the stretchable base layer.

13. The adherent device of claim 12, further comprising a gel patch under each electrode, wherein each gel patch enhances electrical conductivity between its respective electrode and the skin of the subject.

14. The adherent device of claim 12, further comprising a thin, flexible, stretchable overlayer disposed above and adhered to the base layer.

15. An adherent device to monitor a subject having a skin, comprising:
- a stretchable base layer having an upper side and a lower side and an adhesive coating on the lower side to adhere the base layer to the skin of a subject, the base layer having at least two openings extending therethrough, each of the at least two openings having a size;
- a stretchable covering layer positioned above and adhered to the base layer with an adhesive to define at least two pockets, wherein the stretchable covering layer is thin, flexible, and configured to stretch with the skin of the subject;
- a flexible circuit comprising a first portion and a second portion, the first portion of the flexible circuit adhered between the stretchable base layer and the stretchable covering layer, the second portion having a loop shape that extends away from the first portion through an opening in the stretchable covering layer, wherein the first portion of the flexible circuit is formed of a substantially non-stretchable material, and has a serpentine, sawtooth, or other shape that geometrically configures the flexible circuit to be stretchable along a length of the adherent device;
- at least two electrodes in contact with the first portion of the flexible circuit;
- at least two gels, wherein each gel and each electrode are positioned within a corresponding pocket, each gel having a size larger than the size of the respective opening to retain said gel substantially within said pocket between the base layer and the covering layer; and
- a circuit carrier positioned above the stretchable covering layer and supported with the stretchable base layer, the circuit carrier holding electronic components electrically connected to the at least two electrodes with the second portion of the flexible circuit to relieve strain when the stretchable base layer stretches with the skin of the subject, the electronic components configured to measure at least one physiologic signal of the subject.

16. An adherent device to adhere to a skin of a subject, comprising:
- means for adhering to a skin of a subject, the means for adhering comprising a stretchable base layer having an upper side and a lower side and an adhesive coating on the lower side to adhere the base layer to the skin of a subject, the base layer having at least two openings extending therethrough, each of the at least two openings having a size, and the means for adhering further comprising a stretchable covering layer positioned above and adhered to the base layer with an adhesive to define at least two pockets, wherein the stretchable covering layer is thin, flexible, and configured to stretch with the skin of the subject;
- a flexible circuit coupled to the means for adhering, the flexible circuit carrying at least two electrodes disposed on the flexible circuit and positioned to couple to the subject's skin, wherein the flexible circuit further includes a first portion located adjacent to the upper side of the stretchable base layer and a second portion that extends away from the flexible circuit and through an opening in the stretchable covering layer; and means for enhancing electrical conductivity between the electrodes and the subject's skin, a circuit carrier positioned above the stretchable covering layer and coupled to the at least two electrodes via the second portion of the flexible circuit, the circuit carrier holding circuitry to measure at least one physiologic signal of the subject; and a compliant connection that includes a plurality of loops formed between the stretchable base layer and the circuit carrier that permits at least some movement of the circuit carrier in a plane parallel to the stretchable base layer.

17. The adherent device of claim 1, wherein the base layer, the adhesive coating, and the covering layer are coextensive.

18. The adherent device of claim 2, wherein the base layer, the adhesive coating, and the covering layer are coextensive.

19. The adherent device of claim 2, wherein the circuit carrier and the electronic components are comprised in a reusable electronics module.

20. The adherent device of claim 1, wherein the second portion of the flexible circuit includes a loop shape that extends around an outer circumference of one of the plurality of bridging loops.

21. The adherent device of claim 20, wherein the plurality of bridging loops connect to an inner portion of the stretchable base layer to prevent loads from being transferred to a perimeter of the stretchable base layer.

\* \* \* \* \*